United States Patent
Campbell et al.

(10) Patent No.: US 11,803,969 B2
(45) Date of Patent: Oct. 31, 2023

(54) INTRAOPERATIVE IMAGING AND VIRTUAL MODELING METHODS, SYSTEMS, AND INSTRUMENTALITIES FOR FRACTURE REDUCTION

(71) Applicant: DEPUY SYNTHES PRODUCTS, INC., Raynham, MA (US)

(72) Inventors: Christopher Campbell, West Chester, PA (US); Glen Pierson, Glenmoore, PA (US); Beat Lechmann, West Chester, PA (US); Michael Blauth, West Chester, PA (US)

(73) Assignee: DEPUY SYNTHES PRODUCTS, INC., Raynham, MA (US)

( * ) Notice: Subject to any disclaimer, the term of this patent is extended or adjusted under 35 U.S.C. 154(b) by 240 days.

(21) Appl. No.: 17/325,147

(22) Filed: May 19, 2021

(65) Prior Publication Data

US 2021/0366118 A1    Nov. 25, 2021

Related U.S. Application Data

(60) Provisional application No. 63/027,567, filed on May 20, 2020.

(51) Int. Cl.
*G06T 7/00* (2017.01)
*A61B 90/00* (2016.01)
(Continued)

(52) U.S. Cl.
CPC .......... *G06T 7/0014* (2013.01); *A61B 17/68* (2013.01); *A61B 90/36* (2016.02); *A61B 90/37* (2016.02);
(Continued)

(58) Field of Classification Search
CPC .......... G06T 7/0014; G06T 7/344; G06T 7/73; G06T 7/60; G06T 17/00;
(Continued)

(56) References Cited

U.S. PATENT DOCUMENTS 9,508,149 B2    11/2016  Simon et al.
9,554,868 B2 *   1/2017  Regazzoni ............. A61B 34/20
(Continued)

FOREIGN PATENT DOCUMENTS

CN      106963489         7/2017
WO      2015/124171 A1    8/2015

OTHER PUBLICATIONS

Javad Fotouhi et al: "From Perspective X-ray Imaging to Parallax-Robust Orthographic Stitching", arxiv.org, Cornell University Library, 201 Olin Library Cornell University Ithaca, NY 14853, Mar. 6, 2020 (Mar. 6, 2020), XP081615929.

(Continued)

*Primary Examiner* — Shefali D Goradia
(74) *Attorney, Agent, or Firm* — BakerHostetler

(57) ABSTRACT

A method of evaluating a bone fracture reduction includes imaging, intraoperatively, a fractured bone to obtain a representation of the fractured bone in a computing system. The fractured bone defines at least first and second bone fragments separated by a fracture. The method includes imaging a contralateral bone of the patient to obtain a representation of the contralateral bone in the computing system and further includes generating, intraoperatively in the computing system, a virtual model of the fractured bone from data presented in the representation of the fractured bone and a virtual model of the contralateral bone from data presented in the representation of the contralateral bone. The method includes comparing, intraoperatively in the computing system, a spatial dimension measured with respect to the virtual (Continued)

model of the fractured bone with a corresponding spatial dimension measured with respect to the virtual model of the contralateral bone.

20 Claims, 14 Drawing Sheets

(51) Int. Cl.
| | | |
|---|---|---|
| G06T 17/00 | (2006.01) | |
| G06T 7/33 | (2017.01) | |
| G06T 7/73 | (2017.01) | |
| A61B 17/68 | (2006.01) | |
| G06T 7/60 | (2017.01) | |
| A61B 34/10 | (2016.01) | |
| A61B 17/56 | (2006.01) | |

(52) U.S. Cl.
CPC .............. *G06T 7/344* (2017.01); *G06T 7/60* (2013.01); *G06T 7/73* (2017.01); *G06T 17/00* (2013.01); *A61B 2017/564* (2013.01); *A61B 2017/681* (2013.01); *A61B 2034/105* (2016.02); *A61B 2090/363* (2016.02); *A61B 2090/376* (2016.02); *G06T 2207/10028* (2013.01); *G06T 2207/10116* (2013.01); *G06T 2207/20101* (2013.01); *G06T 2207/20212* (2013.01); *G06T 2207/30008* (2013.01); *G06T 2207/30204* (2013.01)

(58) Field of Classification Search
CPC . G06T 2207/10028; G06T 2207/10116; G06T 2207/20101; G06T 2207/20212; G06T 2207/30008; G06T 2207/30204; A61B 90/36; A61B 90/37; A61B 17/68; A61B 2034/105; A61B 2090/363; A61B 2090/376; A61B 2017/564; A61B 2017/681
See application file for complete search history.

(56) References Cited

U.S. PATENT DOCUMENTS

| | | | |
|---|---|---|---|
| 9,610,056 B2 | 4/2017 | Lavallee et al. | |
| 9,980,783 B2 | 5/2018 | Wiets et al. | |
| 10,217,217 B2 | 2/2019 | Dhruwdas | |
| 10,867,436 B2 | 12/2020 | Oved | |
| 2011/0082367 A1* | 4/2011 | Regazzoni | A61B 34/20 600/425 |
| 2016/0100909 A1* | 4/2016 | Wollowick | G16H 40/63 600/424 |
| 2016/0331463 A1* | 11/2016 | Nötzli | A61B 34/10 |
| 2017/0360578 A1* | 12/2017 | Shin | G09B 23/286 |
| 2018/0280090 A1 | 10/2018 | Davies et al. | |
| 2018/0325599 A1 | 11/2018 | Seo | |
| 2019/0122330 A1 | 4/2019 | Saget et al. | |
| 2020/0390503 A1* | 12/2020 | Casas | A61B 34/20 |

OTHER PUBLICATIONS

Mauler Flavien et al: "Prediction of normal bone anatomy for the planning of corrective osteotomies of malunited forearm bones using a three-dimensional statistical shape model : Statistical Shape Model of the Forearm Bones", Journal of Orthopaedic Research, vol. 35, No. 12, May 4, 2017 (May 4, 2017), pp. 2630-2636, XP055820846.

Megan E. Cain et al., Prevalence of Rotational Malalignment After Inramedullary Nailing of Tibial Shaft Fractures: Can We Reliably Use the Contralateral Uninjured Side as the Reference Standard?, 102 J. of Bone and Joint Surgery 582-591 (2020).

Messmer Peter et al: "Image Fusion for Intraoperative Control of Axis in Long Bone Fracture Treatment", European Journal of Trauma, Urban & Vogel, Muenchen, DE, vol. 32, No. 6, Dec. 31, 2006 (Dec. 31, 2006), pp. 555-561, XP035803495.

Schweizer Andreas et al: "Computer-Assisted 3-Dimensional Reconstructions of Scaphoid Fractures and Nonunions With and Without the Use of Patient-Specific Guides: Early Clinical Outcomes and Postoperative Assessments of Reconstruction Accuracy", The Journal of Hand Surgery, W.B. Saunders, Amsterdam, NL, vol. 41, No. 1, Dec. 19, 2015 (Dec. 19, 2015), pp. 59-69, XP029364894.

Gunay et al., Cost- and time-effective three-dimensional bone-shape reconstruction from X-ray images, International Journal of Medical Robotics and Computer Assisted Surgery, 2007; 3: 323-335.

Willis et al, 3D Reconstruction of Highly Fragmented Bone Fractures, 2007, 10 pages.

* cited by examiner

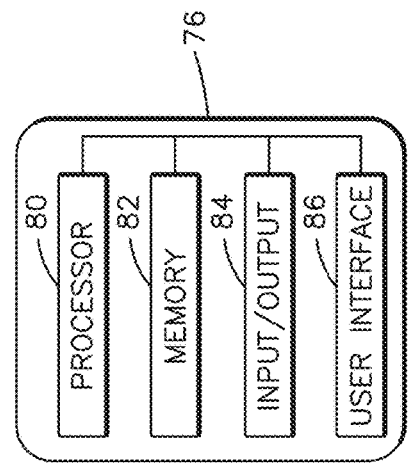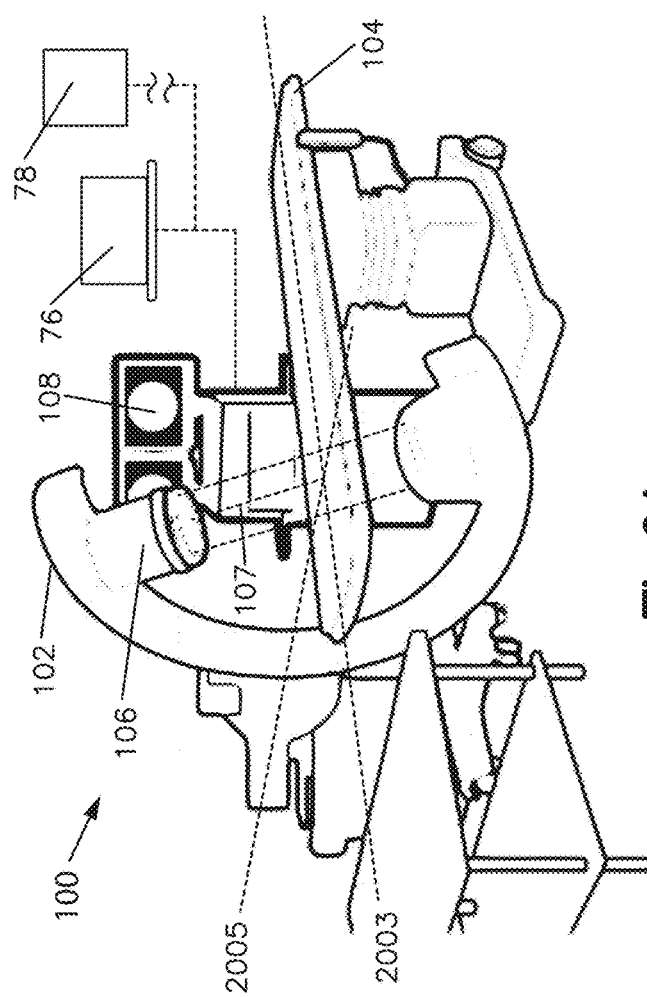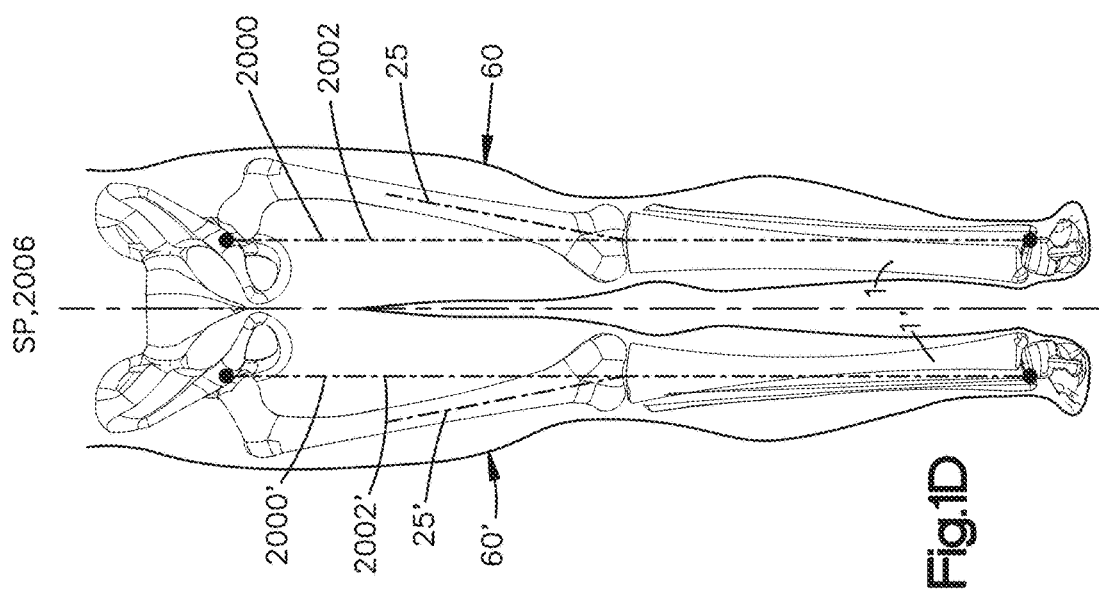

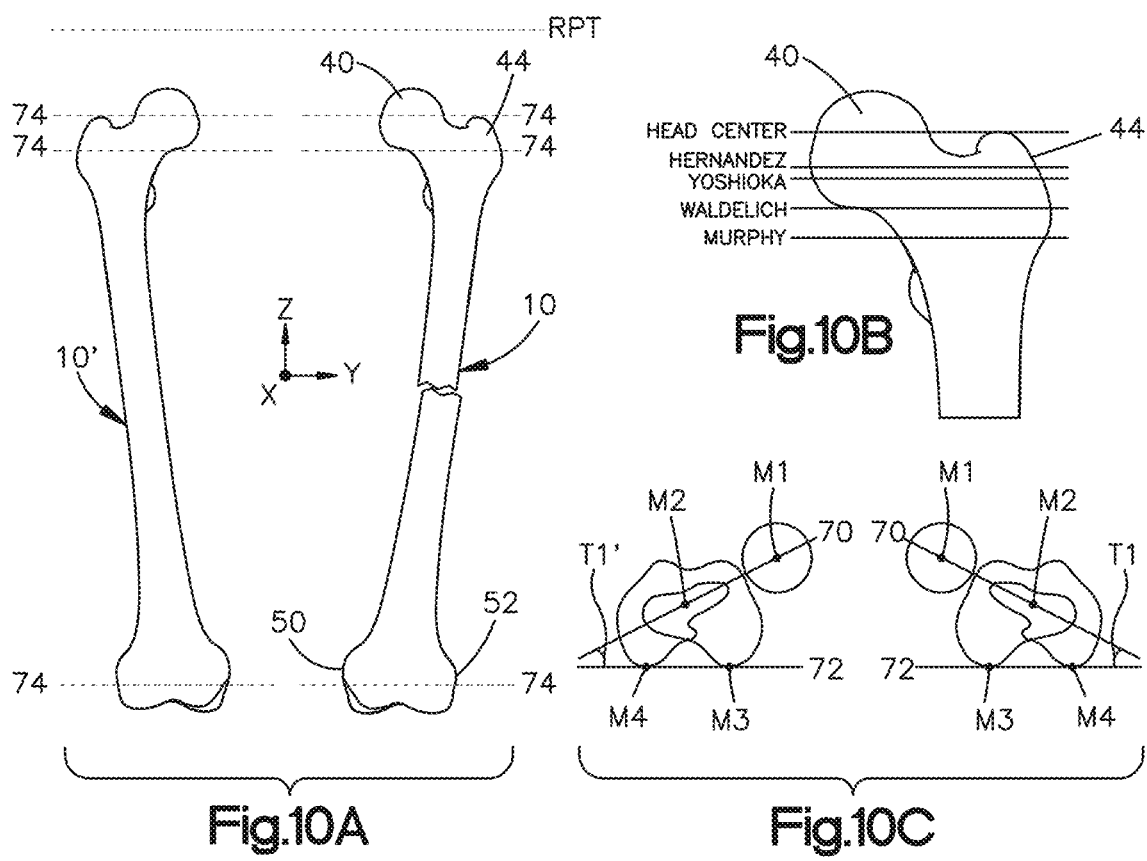
Fig.10A
Fig.10B
Fig.10C
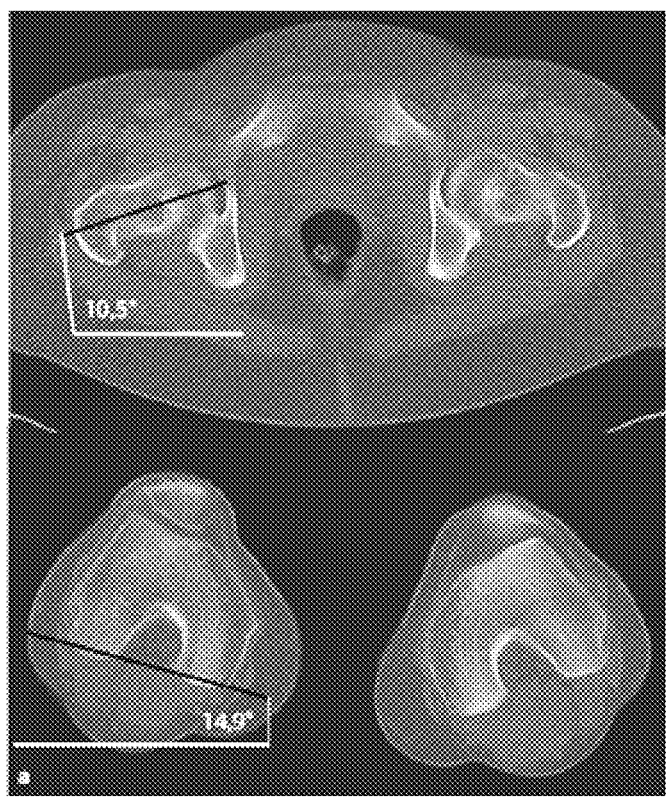
Fig.10D
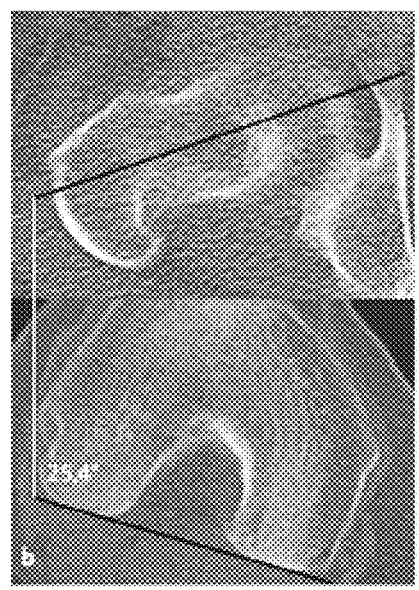
Fig.10E

INTRAOPERATIVE IMAGING AND VIRTUAL MODELING METHODS, SYSTEMS, AND INSTRUMENTALITIES FOR FRACTURE REDUCTION

CROSS-REFERENCE TO RELATED APPLICATIONS

This application claims the benefit of U.S. Provisional Patent Application Ser. No. 63/027,567, filed May 20, 2020, entitled "IMAGE MATCHING FOR FRACTURE REDUCTION," the entire disclosure of which is hereby incorporated by reference herein.

TECHNICAL FIELD

The present disclosure relates to systems and methods of viewing reduced bone fractures.

BACKGROUND

Many dislocated fractures of long bones, such as of the lower extremities, are currently treated surgically (osteosynthesis) by supporting (e.g., joining, fixing, or otherwise stabilizing) bone fragments with implants, such as screws, plates, nails, and/or wires, including entirely internal implants or partially external implants, by way of non-limiting examples. Conventional osteosyntheses typically include preoperative, intraoperative, and postoperative medical imaging. Preoperative and postoperative medical imaging is used for diagnosis and planning, and control, respectively. Intraoperative medical imaging, which is commonly achieved using a mobile fluoroscope, provides an optical feedback to control the manipulation of the fracture fragments, appropriate alignment and implant positioning. However, fluoroscope images have limitations. For example, fluoroscope images tend to be limited to the fracture area only and also tend to be limited in providing imaging information related to the restoration of length, rotation and angulation of the affective bone.

In fractures of the lower limbs there are mainly two treatment options: closed reduction internal fixation (CRIF) and open reduction internal fixation (ORIF), although many treatments include a combination of CRIF and ORIF methodologies. In CRIF the reduction is carried out without direct exposure and direct visualization of the fracture. The only visual information about the fractured bone is provided by intraoperative fluoroscopy and/or clinical signs, although the latter can be unreliable. In contrast, in ORIF, the fracture is exposed surgically by dissecting the overlaying soft tissues. Exposing the fracture, the surgeon can reduce it under direct vision, optionally in combination with fluoroscopic imaging, and subsequently controlling the end result with the fluoroscope.

For many shaft fractures of tibia and femur, CRIF using intramedullary nails is the treatment of choice. In other cases, for instance where closed reduction is impossible or in institutions where no image intensifier is available, ORIF and/or minimally invasive osteosynthesis (MIO) is used. Closed reduction is preferred because it is less invasive, more respectful of soft tissues, it lowers the risk of greater blood loss, interferes less with the biology of fracture healing, and shows better cosmetic results. However, CRIF is technically more demanding for the surgeon and exposes both the patient and the medical staff to higher radiation doses.

Possible complications of fixing the femoral or tibial shaft include angular and/or rotational malalignment of the fracture fragments as well as incorrect restoration of the bone length. Such complications can cause false posture, or restricted movement and/or excessive strain on the patient's joint structures due to a significant change in the natural anatomical structure and biomechanics. In many cases, the above-mentioned complications could be avoided, if improved intraoperative visualization modalities were available. Such improved intraoperative visualization modalities could thus avoid, or at least reduce, the need for postoperative surgical revisions (e.g., weeks, months, or years after surgery) necessitated by malreduction.

SUMMARY

According to an embodiment of the present disclosure, a method includes imaging, intraoperatively, a fractured bone to obtain a representation of the fractured bone in a computing system. The fractured bone defines at least first and second bone fragments separated by a fracture. The method includes imaging a contralateral bone of the patient to obtain a representation of the contralateral bone in the computing system and further includes generating, intraoperatively in the computing system, a 3D virtual model of the fractured bone from data presented in the representation of the fractured bone and a 3D virtual model of the contralateral bone from data presented in the representation of the contralateral bone. The method includes comparing, intraoperatively in the computing system, a spatial dimension measured in the 3D virtual model of the fractured bone with a corresponding spatial dimension measured in the 3D virtual model of the contralateral bone.

According to another embodiment of the present disclosure, a method includes imaging, intraoperatively, a fractured bone to obtain a representation of the fractured bone in a computing system. The fractured bone defines at least first and second bone fragments separated by a fracture. The representation of the fractured bone includes a combined series of images of the fractured bone taken at intervals along a length thereof. The method includes imaging a contralateral bone to obtain a representation of the contralateral bone in the computing system. The representation of the contralateral bone includes a combined series of images of the contralateral bone taken at intervals along a length thereof. The method also includes, intraoperatively in the computing system, measuring a first spatial dimension defined with respect to at least two anatomical landmarks presented in one of the representation of the fractured bone and the representation of the contralateral bone; automatically identifying contralateral counterparts of the at least two anatomical landmarks presented in the other of the representation of the fractured bone and the representation of the contralateral bone; and measuring a second spatial dimension defined with respect to the contralateral counterparts of the at least two anatomical landmarks.

BRIEF DESCRIPTION OF THE DRAWINGS

The following description of the illustrative embodiments may be better understood when read in conjunction with the appended drawings. It is understood that potential embodiments of the disclosed systems and methods are not limited to those depicted.

FIG. 1D is a schematic diagram of the limbs of a lower torso, illustrating various axes of the limbs;

FIG. 2A shows a fracture imaging system according to an example embodiment for implementing steps of the methods of the present disclosure;

FIG. 2B shows a computing system according to one example that can be used to implement various steps of the methods of the present disclosure;

FIGS. 10A-10C show example steps of using corresponding 3D models of the fractured bone and contralateral bone to calculate a malalignment torsion parameter of the fractured bone by comparison to the contralateral bone, according to the example method shown in FIG. 3A;

FIGS. 10D-10E show example steps of using medical imagery of the fractured bone and contralateral bone to calculate a malalignment torsion parameter of the fractured bone by comparison to the contralateral bone, according to another example method of the present disclosure;

DETAILED DESCRIPTION OF ILLUSTRATIVE EMBODIMENTS

Figure 1A:
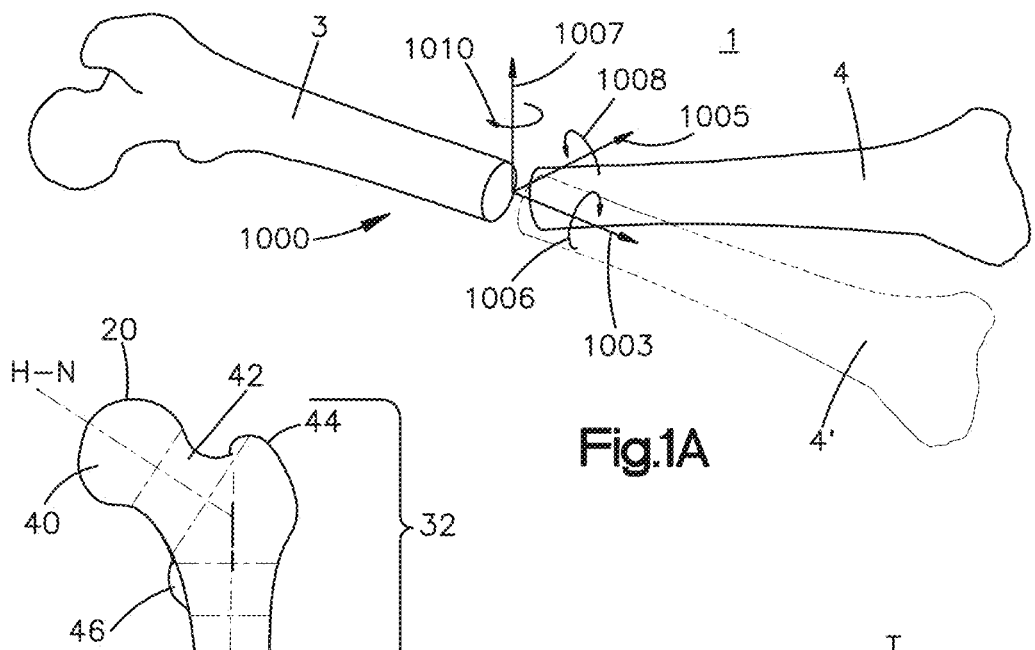
FIG. 1A is a schematic perspective view of a fractured bone having a proximal bone fragment and a distal bone fragment with a correct orientation of the distal bone fragment shown in phantom.

Conventional osteosynthesis systems and processes lack the capability to provide accurate, computational, intraoperative evaluation of fracture reduction, particularly during closed reduction internal fixation (CRIF). Intraoperatively, surgeons typically evaluate fracture reductions by way of visual inspection (including via fluoroscopy), a technique commonly referred to as "eye-balling" the reduction. However, mere visual inspection of a reduced fracture rarely provides a surgeon with accurate, measureable parameters to fully evaluate the overall reduction, including whether the reduction has restored the length, rotation, and angulation of the repaired bone or segments thereof. One reason for these shortcomings is because fluoroscopic imaging typically only provides short-segmented visualization of long bones (e.g., femur, tibia, fibula, humerus, radius, ulna). Fracture zones may additionally increase the difficulty of visual orientation via fluoroscopy. Visual inspection of the patient is often further impeded by surgical sterile coverage of parts of the extremities. For example, the uninjured contralateral side of the patient is usually not scrubbed and thus not accessible during surgery. Preferably, the whole bone in question should be visible, either on the screen or at the patient, but such visualization is difficult to achieve with current medical imaging systems. The foregoing challenges have contributed to a prevalence of malalignment during bone reduction surgeries. For example, in one recent study, of 154 patents who were treated for a unilateral tibial shaft fracture with an intramedullary (IM) nail and then postoperatively evaluated via low-dose bilateral CT imagery, more than one third of those patients (specifically, 55 patients, 36% of the observed group) had postoperative rotational malalignment of $\geq 10°$. Megan E. Cain et al., *Fractures: Can We Reliably Use the Contralateral Uninjured Side as the Reference Standard?*, 102 J. of Bone and Joint Surgery 582 (2020).

The methods, systems, and features described herein employ medical imaging equipment (e.g., fluoroscopy equipment) to provide intraoperative measurements, in real-time, comparing the length, rotation, and angulation of the repaired bone to those of a virtual two-dimensional (2D) or three-dimensional (3D) model of a non-fractured rendition of the bone. These comparative measurements allow the surgeon to assess, intraoperatively, whether further reduction and/or manipulation of the reduced bone segments is warranted. The virtual model of the non-fractured rendition of the bone is created from images of the patient's contralateral bone. As used herein, the term "contralateral" refers to the corresponding bone on the opposite side of the body along the medial-lateral direction. For example, if the fractured bone is the patient's right femur, then the contralateral bone is the patient's left femur.

It should be appreciated that during conventional osteosyntheses, preoperative imaging and planning do not address the aforementioned challenges relating to evaluation of fracture reductions. Furthermore, preoperative imaging can have several drawbacks. For example, preoperative imaging and planning consumes valuable time that might be needed in cases of more urgent fracture reductions. Also, the time consumed by preoperative imaging and planning could otherwise be used by the medical professional to treat other patients. As another example, preoperative imaging can result in additional radiation exposure for medical professionals and patients that could otherwise be avoided if preoperative imaging were eliminated. As yet another example, a patient's anatomy can change between preoperative imaging/planning and the actual reduction procedure. For instance, bone fragments can move relative to one another due to general settling of the bone fragments or due to movement of the patient from, for example, a preoperative setting to an operating room, or from a hospital bed to an operating table. Failure to take into account such changes can result in improper fracture reduction. Alternatively, taking into account such changes can increase the amount of time needed to reduce the fracture. By providing accurate, comparative intraoperative measurements of the repaired bone, the methods and systems described below can avoid shortcomings stemming from overreliance on preoperative imaging and planning for osteosyntheses, and can further provide intraoperative evaluation of whether a surgical plan has been satisfactorily achieved.

Referring initially to FIG. 1A, one example of a fractured bone 1 is illustrated. In this particular example, the bone 1 is a long bone, and the fracture is located along a diaphysis (i.e., shaft) of the bone 1. The fractured bone 1 has a proximal bone fragment 3 separated from a distal bone fragment 4. In the illustrated example, the bone 1 is a femur, although it should be appreciated that the bone 1 can include, but is not necessarily limited to, bones in the leg such as the femur and tibia, or bones of the arm such as the humerus, the ulna, and the radius. It will be understood that the bone 1 could be a bone other than a long bone, such as a rib or clavicle, and the fracture can be located on a portion of the bone other than the shaft such as on the epiphysis or metaphysis. An outline of the distal bone fragment 4' in the desired anatomical position is indicated in a dashed line. An offset between the proximal bone fragment 3 and the distal bone fragment 4 can be defined by a system of coordinates 1000. The coordinates 1000 include a longitudinal axis 1003 that extends generally parallel to the fractured bone when in a non-fractured state, a lateral axis 1005 that extends substantially perpendicular to the longitudinal axis 1003, and a transverse axis 1007 that extends substantially perpendicular to the longitudinal axis 1003 and the lateral axis 1005. The longitudinal axis 1003 is oriented along a longitudinal direction L, the lateral axis 1005 is oriented along a lateral direction A, and the transverse axis 1007 is oriented along a transverse direction T.

Intraoperatively, the reduction of the malalignment can be performed with respect to a number of degrees of freedom, including up to six (6) degrees of freedom. For instance, with regard to reduction according to specific degrees of freedom, the distance between the bone fragments 3 and 4 along the longitudinal axis 1003 may be shortened or lengthened. Deviations in the angular direction 1006 about longitudinal axis 1003 may be adjusted via external or internal rotation of one or both bone fragments 3 and 4. Deviations in the angular direction 1008 about lateral axis 1005 may be adjusted via external or internal rotation of one or both bone fragments 3 and 4. Deviations in the angular direction 1010 about transverse axis 1007 may be adjusted via external or internal rotation of one or both bone fragments 3 and 4. It should be appreciated that the degrees of freedom involved in a reduction can vary based on a number of factors, including the type, location, and severity of fracture, the number of bone fragments resulting from the fracture, and the implant and/or instrumentation employed to reduce and/or fix the fracture. For example, if an IM nail is employed, lateral translation of one or more bone fragments along lateral axis 1005 can be limited, thereby reducing the subsequent number of degrees of freedom involved in the reduction.

Figure 1B:
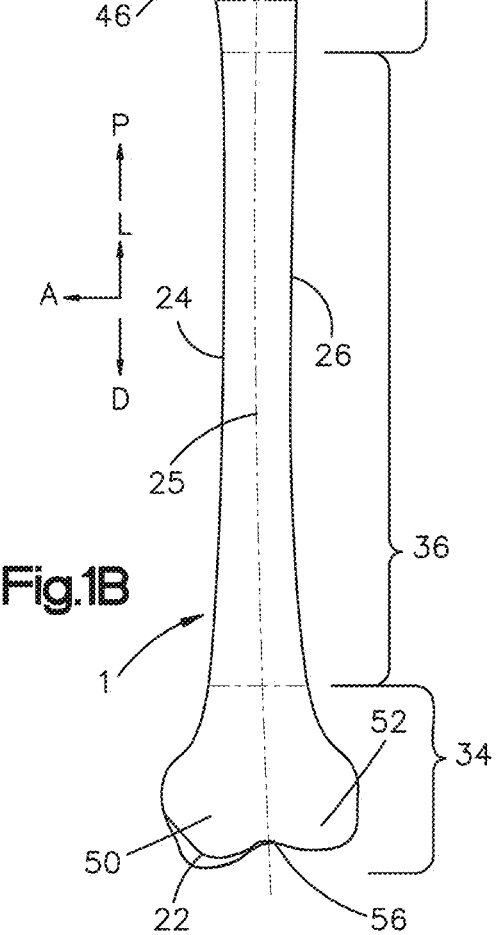
FIG. 1B is an anterior view of a femur, illustrating various anatomical portions of the femur.
Figure 1C:
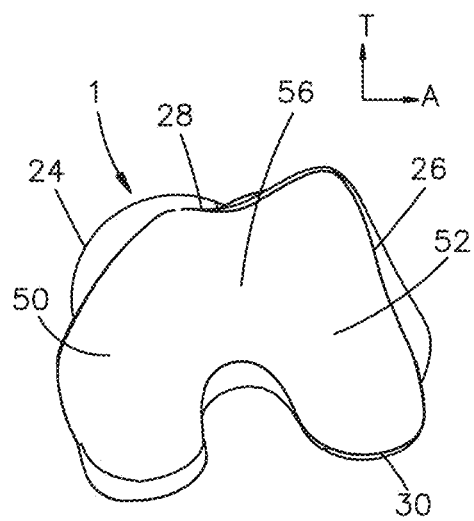
FIG. 1C is a bottom, transverse view of the femur illustrated in FIG. 1B.

Referring now to FIGS. 1B and 1C, the bone 1 of the illustrated example (i.e., femur) has anatomical proximal and distal ends 20, 22 spaced from each other along the longitudinal direction L, which is oriented along an anatomical axis 25 of the bone 1 that generally extends along the intramedullary canal thereof. It should be appreciated that, when the bone 1 is a femur or tibia, the longitudinal direction L is generally oriented along the cranial-caudal direction of patient anatomy. The proximal end 20 is spaced from the distal end 22 in a proximal direction P, while the distal end 22 is spaced from the proximal end 20 in a distal direction D that is opposite the proximal direction P. It should be appreciated that the proximal and distal directions P, D are each mono-directional components of the longitudinal direction L, which is bi-directional. The bone 1 has a medial side 24 and a lateral side 26 spaced from each other along the lateral direction A, which is oriented along the medial-lateral direction of patient anatomy. In particular, the medial side 24 is spaced from the lateral side 26 in the anatomical "medial direction," and the lateral side 26 is spaced from the medial side 24 in the anatomical "lateral direction." It should be appreciated that, as used herein, the term "lateral direction A" is bi-directional and encompasses the mono-directional medial and lateral directions of patient anatomy. The femur 1 also has an anterior side 28 and a posterior side 30 spaced from each other along the transverse direction T, which is oriented along the anterior-posterior direction of patient anatomy. In particular, the anterior side 28 is spaced from the posterior side 30 in the anatomical "anterior direction," and the posterior side 30 is spaced from the anterior side 28 in the anatomical "posterior direction." It should be appreciated that, as used herein, the term "transverse direction T" is bi-directional and encompasses the mono-directional anterior and posterior directions of patient anatomy. The lateral and transverse directions L, T are each substantially perpendicular to each other and are both offset from the longitudinal direction L.

For purposes of the following disclosure, reference will be made to various anatomical regions of the femur 1, including a proximal region 32, a distal region 34, and a shaft region 36 that extends between the proximal and distal regions 32, 34. It should be appreciated that the proximal region 32 is also referred to herein as the "proximal" portion of the respective bone 1 (e.g., "proximal femur"; "proximal humerus"; "proximal tibia"; etc.); the distal region 34 is also referred to herein as the "distal" portion of the bone 1 (e.g., "distal femur", "distal humerus", "distal tibia", etc.); and the shaft region 36 is also referred to herein as the "shaft" of the bone 1.

It should also be appreciated that the proximal and distal regions 32, 34 of the bone 1 each include a plurality of sub-regions and/or features. For example, with respect to the femur 1, the proximal portion 32 thereof (i.e., the "proximal femur" 32) includes a femoral head 40, an intracapsular region which includes a femoral neck 42, a trochanteric region which includes a greater trochanter 44, a transtrochanteric region which includes a lesser trochanter 46, and a subtrochanteric region which extends 5 cm below the lesser trochanter 46 in the distal direction D. The outer surface of the femoral head 40 defines an articular surface of the proximal joint (i.e, the hip joint in this example). The distal portion 34 of the femur 1 (i.e., the "distal femur" 34)

includes medial and lateral condyles 50, 52 that define an articular surface of the joint (i.e., the knee joint in this example), and an intercondylar region that defines an intercondylar notch 56.

Referring now to FIG. 1D, the mechanics of a limb 60 in which the bone 1 resides are illustrated according to one example. In this example, the mechanics are shown relative to a leg. However, it will be understood that the mechanics can apply to other limbs, such as an arm. The limb 60 can be defined by at least one axis, such as a plurality of axes. The at least one axis of the limb 60 can comprise a mechanical axis 2000 of the limb 60 that extends from a center of a head of the limb, such as the femoral head 40 or humeral head, to a center of the opposing joint, such as the ankle or wrist joint. Each long bone of the limb 60 can have a respective mechanical axis 2002 that generally extends from a center of one end of the bone to a center of the other end of the bone. For example, the mechanical axis 2002 of the femur 1 extends from a center of the femoral head 40 to the intercondylar notch 56 of the distal femur 34. Each long bone of the limb 60 also defines a respective anatomical axis 25 that need not be coextensive with the respective mechanical axis 2002 of the bone. For example, the anatomical axis 25 of the femur 1 is angularly offset from the mechanical axis 2002 thereof, as shown. It should be appreciated that the bones can define one or more additional axes. For example, as shown in FIG. 1B, the head 40 and neck 42 of the femur 1 extend along a head-neck axis H-N that is offset from the anatomical axis 25 of the femur 1 at an acute angle.

The at least one axis can be used to determine proper alignment of the mechanics of a limb 60 during fracture reduction. For example, the fractured bone or limb can be manipulated until the fragments of the bone align along a particular mechanical axis 2002 or anatomical axis 25 of the fractured bone. As another example, one or more axes 2002, 25, 2000 of the fractured bone 1 or limb 60 can be compared to a corresponding axis 2002', 25', 2000' of the contralateral bone 1' or limb 60' to evaluate whether the fragments of the fractured bone 1 are properly positioned and oriented during the repair. By way of a non-limiting example, the mechanical axes 2002, 2002' of the fractured bone 1 and the contralateral bone 1' can be employed as primary reference features for evaluating alignment parameters of the fractured bone 1 during the repair. These alignment parameters can include one or more of: (1) a length L1 of the fractured bone 1 measured along the mechanical axis 2002; (2) an angulation A1 of the mechanical axis 2002 relative to its proper orientation; and (3) rotation A2 (i.e., angular position or torsion) of the fractured bone 1 about the proper mechanical axis. It should be appreciated that one or more additional reference features, such as the sagittal plane SP and/or a central longitudinal axis 2006 of the body (i.e., the axis extending along the intersection of the sagittal and coronal planes), can be employed in the foregoing evaluation.

Referring now to FIG. 2A, a fracture reduction system 100 is shown according to one example that can be used to implement steps of the methods described herein. The fracture reduction system 100 can comprise a computing system 76 and an imaging device 102 in electrical communication with the computing system 76. The imaging device 102 can be an x-ray machine, such as a "C-arm", or any be any other suitable imaging device that generates, for example, x-rays, fluoroscopic images (i.e., a stream of x-ray images), CT scans, or ultrasound images. The imaging device 102 is depicted as a C-arm having a single x-ray tube; however, in other embodiments, the imaging device 102 can include two x-ray tubes that are positioned at a fixed angle relative to one another or non-fixed relative to one another. In other words, examples of the disclosure are not limited to a particular configuration of a C-arm x-ray machine.

The fracture reduction system 100 can include an operating bed or table 104 on which the patient lies during the fracture reduction. Unlike some conventional fracture reduction procedures, the operating table 104 need not have coordinates marked thereon to perform the fracture reduction. The imaging device 102 is preferably configured to adjust its field of view (FOV) relative to the table 104 (and thus also relative to the patient thereon). For example, the C-arm 102 can include an x-ray emitter 106 that emits x-rays along a FOV centered along a center beam 107 and is translatable relative to the table 104 along a longitudinal imager axis 2003 along the length of the table 104. The emitter 106 is also preferably rotatable about the longitudinal imager axis 2003, such as for taking x-rays at selective angles relative to patient anatomy, such as along the anterior-posterior direction, lateral direction, and/or various oblique directions, as needed. The emitter 106 can also be translatable relative to the table 104 along a lateral imager axis 2005 that is substantially perpendicular to the longitudinal imager axis 2003. The fracture reduction system 100 can include a display 108, which can include one or more monitors configured to display x-ray and/or fluoroscopic images obtained by the C-arm.

Turning to FIG. 2B, a schematic diagram of the computing system 76 is shown according to one example that can be used to implement steps of the methods described herein. The computing system 76 can be a tablet, a desktop computer, a laptop, a server, or any other suitable computing system. The computing system 76 is configured to transmit x-ray images to the display 108 for viewing. The computing system 76 can include at least one processor 80, a memory 82, and an input/output device 84. It should be appreciated that the at least one processor 80, memory 82, and input/output device 84 can be configured to execute software for processing DICOM files, particularly for reading and extrapolating the various data therein, including, for example, DICOM header data and image data (e.g., image acquisition parameters, image dimensions, pixel intensity, matrix size, and the like) as needed to enhance the methods and steps described below. In some examples, the computing system 76 can include a user interface (UI) 86. The at least one processor 80, memory 82, input/output device 84, and user interface 86 can be coupled together to allow communications therebetween. As should be appreciated, any of the above components may be distributed across one or more separate devices and/or locations.

In various embodiments, the input/output device 84 includes a receiver for receiving data, such as images from an imaging machine, a transmitter for transmitting data, or a combination thereof. The input/output device 84 can be capable of communicating, such as receiving and/or transmitting information pertaining to a communications network such as, for example, the Internet or an Intranet. The communications can be transmitted over, for example, a wired or wireless communications channel, such as for communicating data with additional computing systems, remote servers, and cloud-based applications. As should be appreciated, transmit and receive functionality may also be provided by one or more devices external to the computing system 76.

The at least one processor 80 can include a single processor or more than one processor. Depending upon the exact configuration and type of processor, the memory 82 can be volatile (such as some types of RAM), non-volatile (such as ROM, flash memory, hard disk drive, etc.), or a combination thereof. The computing system 76 can include additional storage (e.g., removable storage and/or non-removable storage) including, but not limited to, tape, flash memory, smart cards, CD-ROM, digital versatile disks (DVD) or other optical storage, magnetic cassettes, magnetic tape, magnetic disk storage or other magnetic storage devices, universal serial bus (USB) compatible memory, or any other medium which can be used to store information. The memory 82 can have instructions stored thereon that, upon execution by the at least one processor 80, cause the computing system 76 to perform various steps of the methods described herein.

The user interface 86 can include inputs that provide the ability to control the computing system 76, via, for example, buttons, soft keys, a mouse, voice actuated controls, a touch screen, movement of the computing system 76, visual cues (e.g., moving a hand in front of a camera on the computing system 76), audio cues, or the like. The user interface 86 may also include, for example, a scanner for scanning of information such as bar codes, QR codes, and RFID tags. The user interface 86 can provide outputs, including visual information (e.g., via a display, a touch screen, or at least one light), audio information (e.g., via speaker), mechanically (e.g., via a vibrating mechanism), or a combination thereof.

Figure 3A:
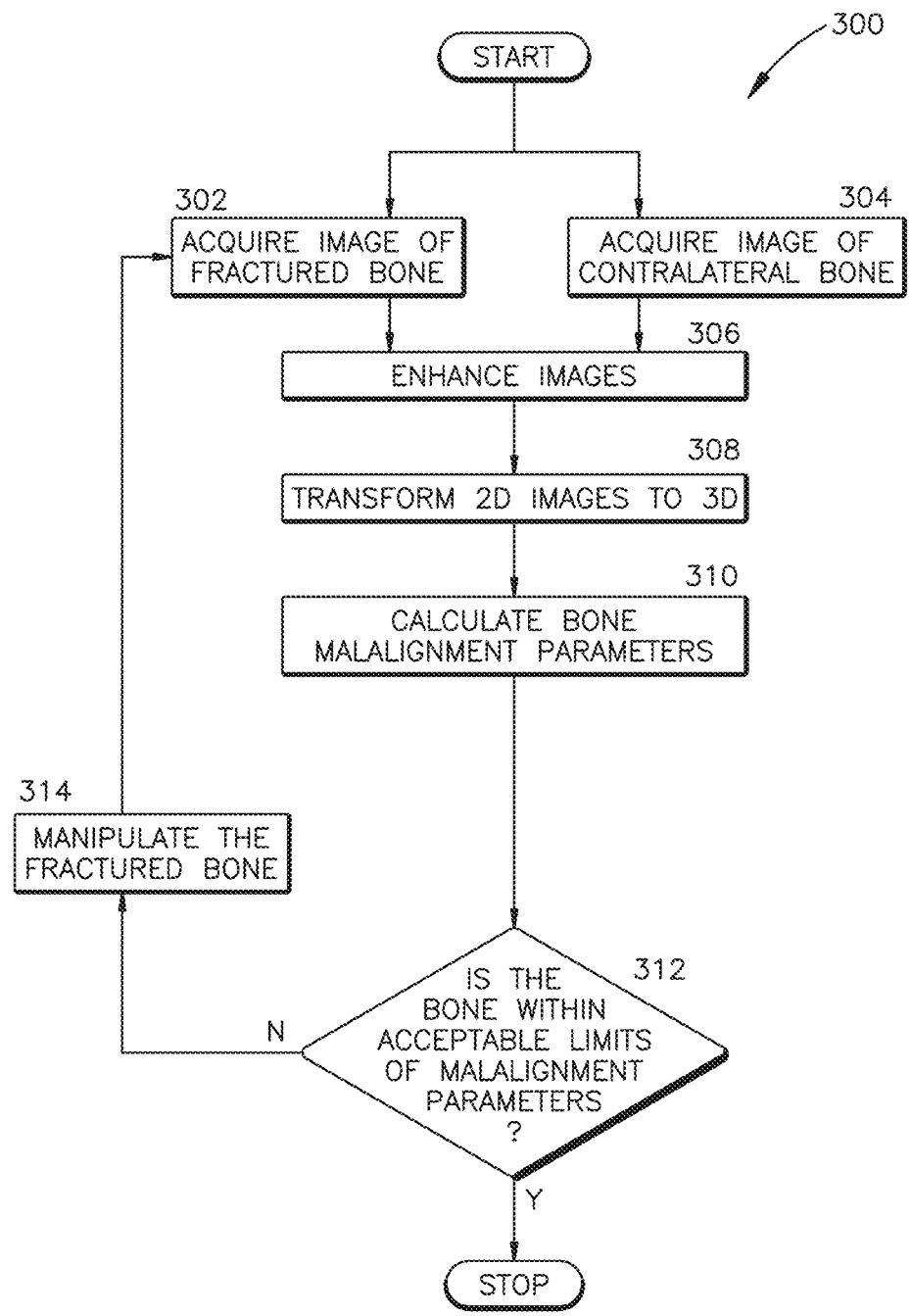
FIG. 3A shows a simplified flow diagram of a method of intraoperatively reducing a malalignment of a fractured bone of a patient, according to one example.

Turning now to FIG. 3A, a method 300 of intraoperatively reducing a malalignment of a fractured bone 1 of a patient is shown according to one example. The method 300 will be described with reference to the fractured femur 1 shown in FIG. 3B, which depicts a fracture 58 of the femoral shaft 36, particularly a midshaft fracture 58 of the patient's left femur 1, shown in relation to the contralateral femur 1' (i.e., the patient's right femur in this example). It should be appreciated, however, that the method 300 can be performed for other fractures, including the fracture shown in FIG. 1A or for any of the fractures discussed herein. The method comprises a step 302 of imaging, intraoperatively, the fractured bone to obtain a first representation 5 of the fractured bone 1 in the computing system 76. As used herein, the terms "intraoperative," "intraoperatively," and derivatives thereof refer to the performance of a step or procedure during the course of a surgical operation. In one example, the terms "intraoperative," "intraoperatively," and derivatives thereof can refer a step or procedure that is performed while the patient is in the operating room in which the fracture reduction is performed. In other words, the terms "intraoperative," "intraoperatively," and derivatives thereof excludes steps or procedures that are performed before the patient is moved to the operating room in which the fracture reduction is performed.

Figure 3B:
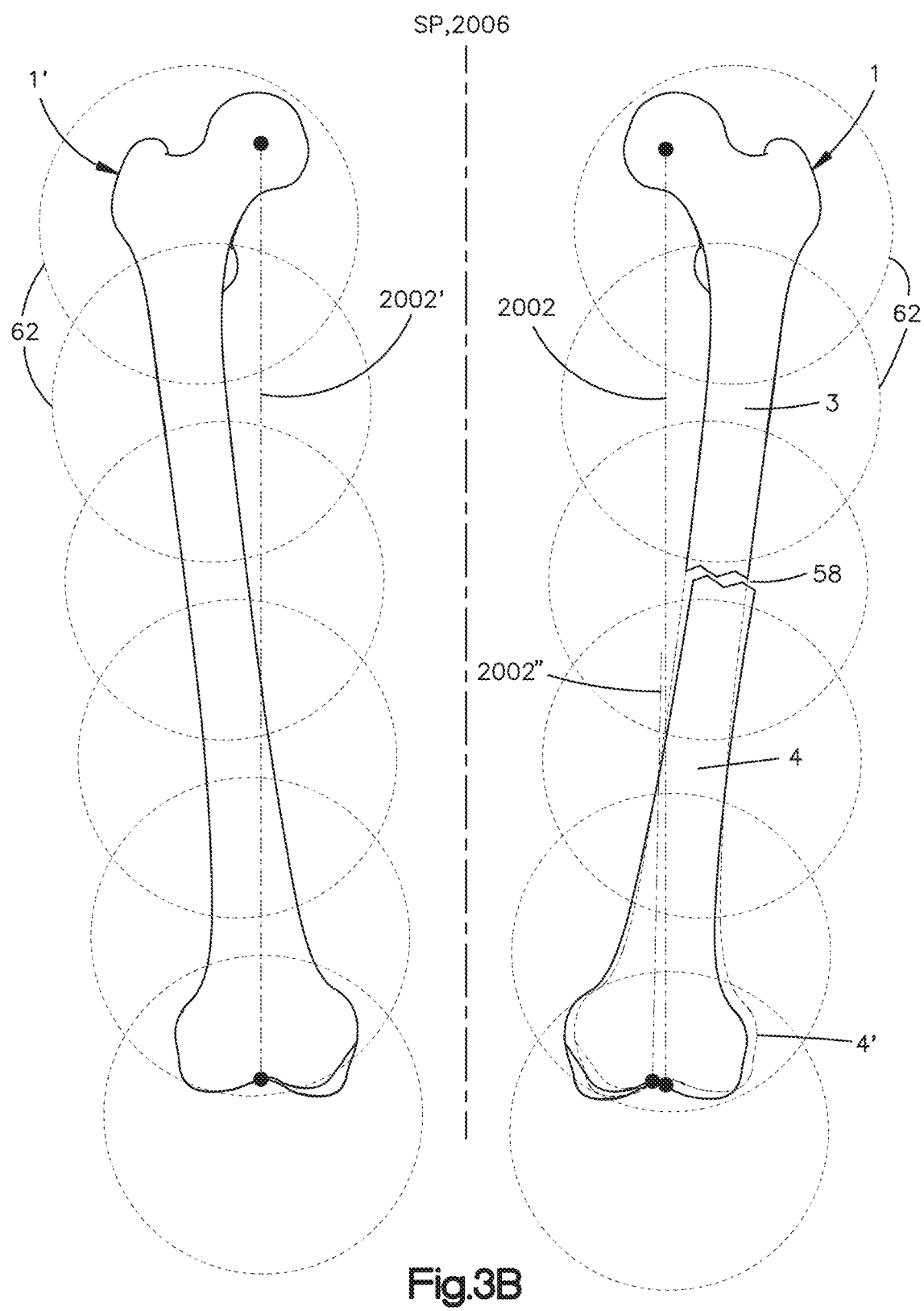
FIG. 3B is an anterior view of a fractured femur and a contralateral, nonfractured femur, with example fluoroscopic image fields indicated by dashed circles, according to example steps of the method illustrated in FIG. 3A.
Figure 3C:
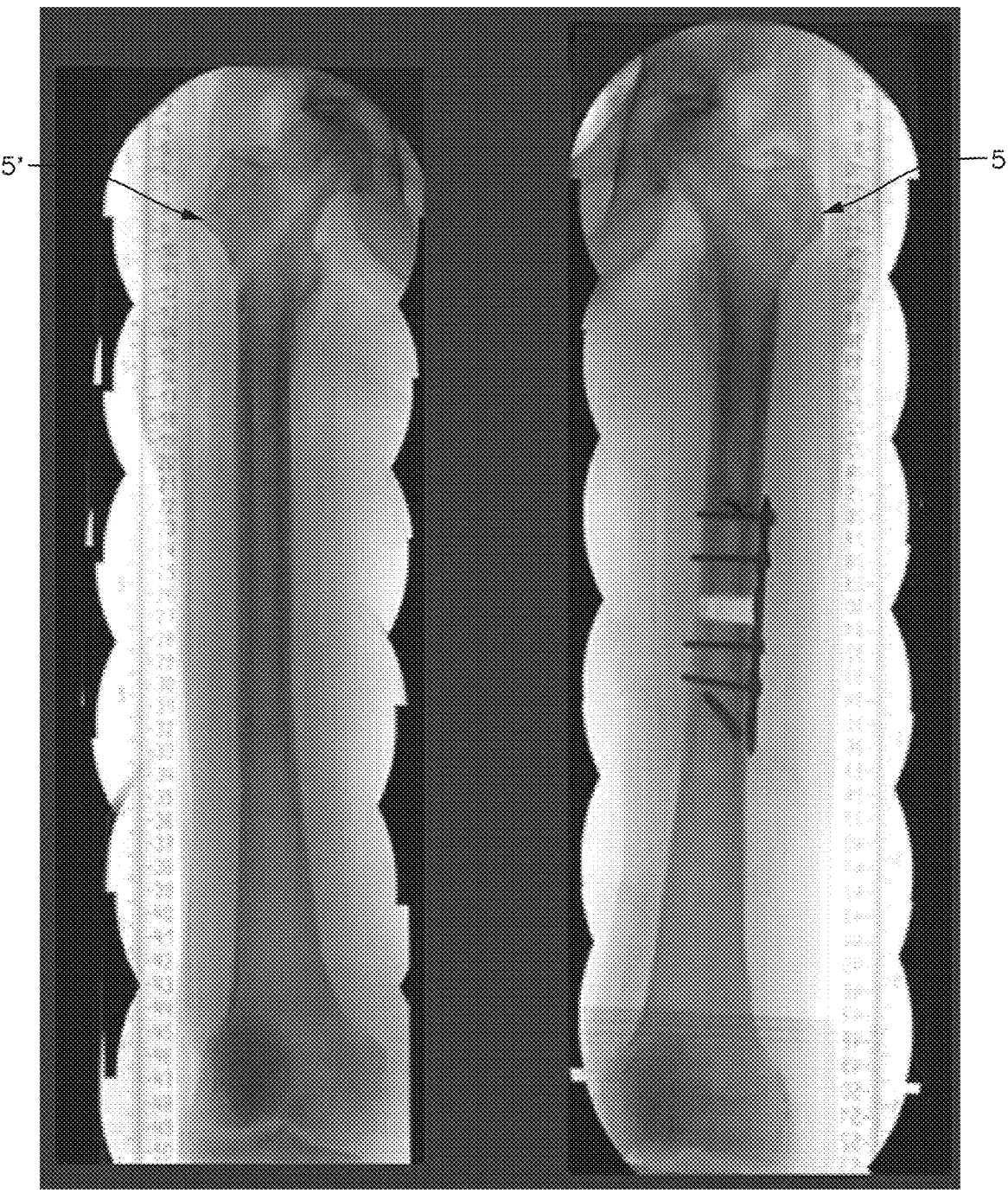
FIG. 3C shows an example of medical imagery constructed from stitched series of images taken along respective intervals of a fractured bone and the contralateral bone to provide full-length images of the bones, which imagery can be used to implement various steps of the methods of the present disclosure.

Step 302 preferably comprises obtaining a full-length image of the fractured bone 1, such that the first representation 5 of the fractured bone 1 preferably comprises the entire length thereof, as shown in FIG. 3C. The length is preferably measured along the mechanical axis 2002 of the bone 1, although the length can alternatively be measured along the anatomical axis 25. The mechanical axis 2002 of the fractured bone 1 is preferably measured between the corresponding landmarks used with reference to the contralateral bone 1'. In the illustrated example, the mechanical axis 2002 of the fractured femur 1 extends between a first or proximal landmark M1 located at a centroid of the femoral head 40 and a second or distal landmark M2 located at the intercondylar notch 56. As shown in FIG. 3B, the presence of the fracture 58 can cause displacement between the proximal and distal bone fragments 3, 4, thereby causing the mechanical axis 2002 to deviate from its proper position and/or orientation, as indicated by axis 2002", which is shown for illustrative purposes.

Step 302 can comprise imaging the fractured bone 1 one or more times to obtain one or more images of the fractured bone 1. The one or more images can comprise x-ray images, CT images or "slices", ultrasound images, and/or any other suitable medical images. The one or more images can comprise a plurality of images 62 of discrete portions of the fractured bone 1, which can be combined, such as by image stitching, to produce the full-length image of the bone 1. For example, the plurality of images 62 can comprise a first image series taken at intervals along the bone length, such as along the mechanical axis 2002, at a first image angle relative to the fractured bone 1. By way of a non-limiting example, the first image series can be taken such that the center beam 107 is aligned along the anterior-posterior direction, thereby providing anterior-posterior views along the length of the fractured bone 1. The plurality of images 62 can also include a second image series taken at intervals along the bone length at a second image angle relative to the fractured bone 1, different from the first image angle. By way of a non-limiting example, the second image series can be taken such that the center beam 107 is aligned along the lateral-medial direction, thereby providing lateral views along the length of the fractured bone 1. As in the foregoing examples, the first and second image series can be taken at angles that are substantially perpendicular to one another, although other relative image angles are possible. In yet another non-limiting example, the second image series can be a series of CT slices that are substantially perpendicular to the anatomical axis of the fractured bone 1.

The method 300 comprises a step 304 of imaging, intraoperatively, the contralateral bone 1' to obtain a second representation 5' of the contralateral bone 1' in the computing system 76. Step 304 preferably comprises obtaining a full-length image of the contralateral bone 1', such that the second representation 5' of the contralateral bone 1' preferably comprises the entire length thereof. The length is preferably measured along the mechanical axis 2002' of the contralateral bone 1', although the length can alternatively be measured along the anatomical axis 25'. As described above, the mechanical axis 2002' of the contralateral bone 1' is preferably measured between the corresponding landmarks used for the fractured bone 1, such as a first or proximal landmark M1 located at a centroid of the femoral head 40 and a second or distal landmark M2 located at the intercondylar notch 56 of the contralateral bone 1'. As with the fractured bone 1, step 304 can comprise imaging the contralateral bone 1' one or more times to obtain one or more images of the contralateral bone 1'. The one or more images can comprise x-ray images, CT images, ultrasound images, and/or any other suitable medical images. The one or more images can comprise a series of images 62 of discrete portions of the contralateral bone 1', which can be combined, such as by image stitching, to produce the full-length image of the contralateral bone 1'. For example, the plurality of images 62 can comprise a third image series taken at intervals along the bone length, such as along the mechanical axis 2002, at a third image angle relative to the contralateral bone 1'. By way of a non-limiting example, the third image series can be taken so as to provide anterior-posterior views along the length of the contralateral bone 1'. The plurality of images 62 can also include and a fourth image series taken at intervals along the bone length at a fourth image angle relative to the contralateral bone 1', different from the third angle. By way of a non-limiting example, the fourth image series can be taken so as to provide lateral views along the length of the contralateral bone 1'. The third and fourth image angles can be substantially perpendicular to one another, although other relative image angles are possible. For example, the fourth image series can be a series of CT slices that are substantially perpendicular to the anatomical axis of the contralateral bone 1'. Preferably, the third and fourth image angles correspond to the first and second image angles, respectively.

Figure 4:
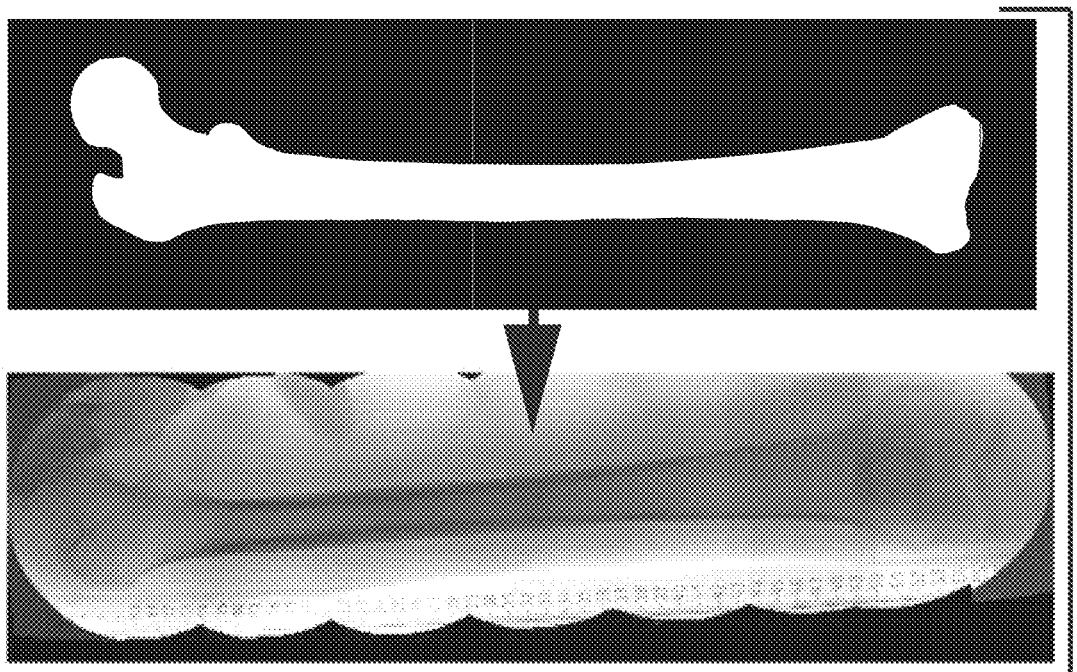
FIG. 4 shows an example of a masking technique for enhancing the medical imagery illustrated in FIG. 3C, as a step of the example method illustrated in FIG. 3A.
Figure 6E:
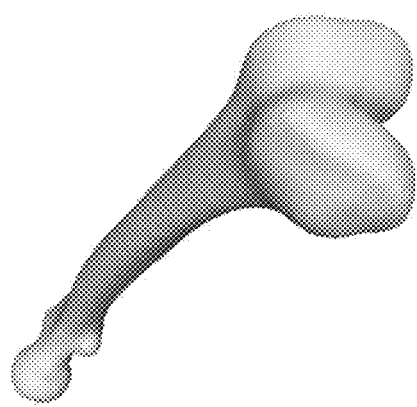
FIGS. 6A-6E show an example of a subsequent rendition of the 3D model of the femur, based on the 3D models shown in FIGS. 5A-5B.
Figure 6D:
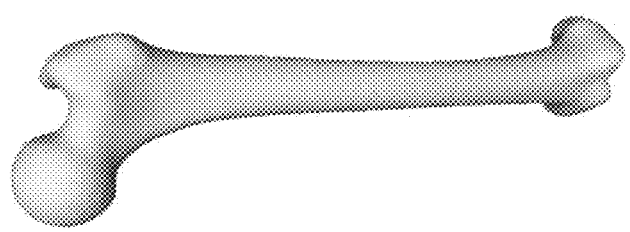
Figure 6C:
Figure 6B:
Figure 6A:
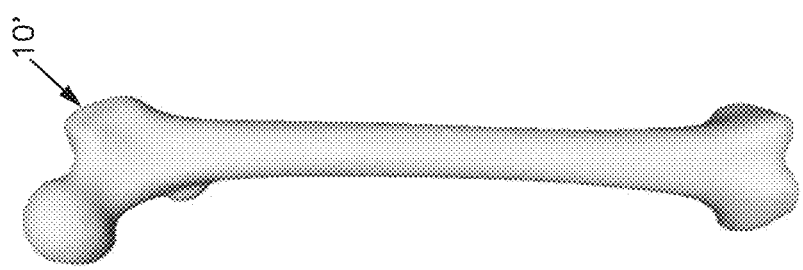
Figure 7E:
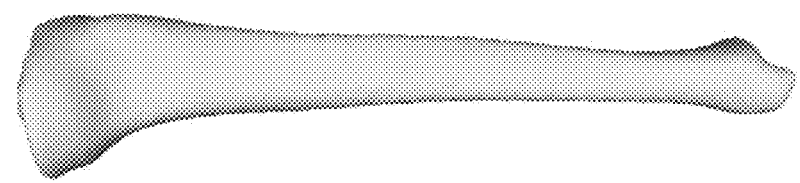
FIGS. 7A-7E show an example of a rendition of a 3D model of a tibia similar to the models of the femur shown in FIGS. 6A-6E.
Figure 7D:
Figure 7C:
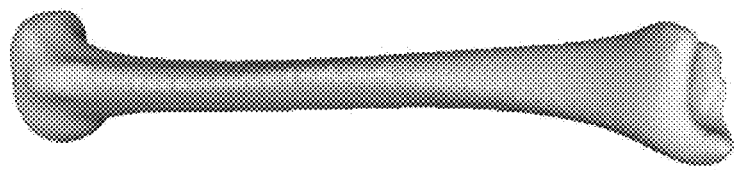
Figure 7B:
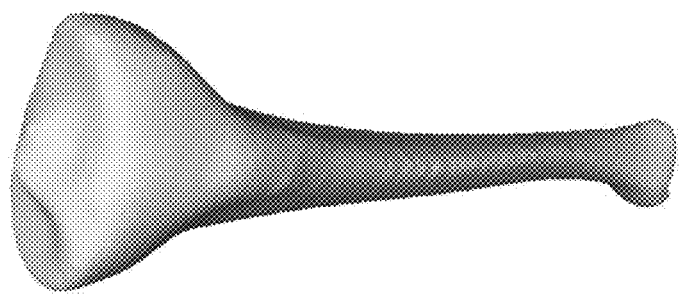
Figure 7A:
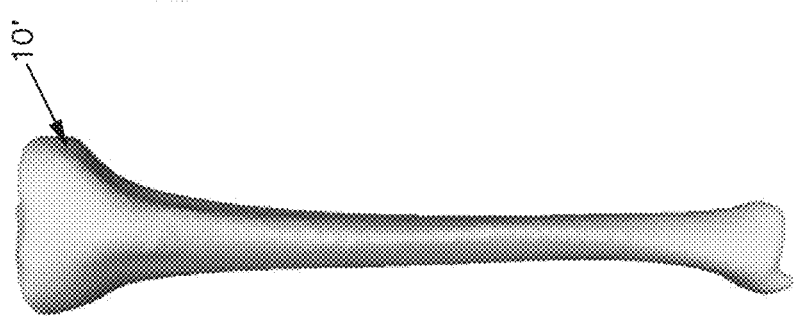

The method 300 comprises a step 306 of enhancing the images of the first representation 5 of the fractured bone 1 and the second representation 5' of the contralateral bone 1'. The image enhancements of step 306 can include substeps that address challenges presented in the images acquired during steps 302, 304. One such challenge can include image drift, which can be caused by radiation distortion resulting from beam divergence toward the periphery of the beam. If unaddressed, image drift can result in distortions between the images of series, which can negatively affect the ability to stitch the series together. Image drift from radiation distortion can be mitigated by employing a compensation algorithm. Another such challenge can include grey graduations or other contrast irregularities between the images in a series. Such contrast graduations can result from auto-adjust contrast modes commonly utilized by physicians. Grey graduations between images can cause data noise in the images and negatively impact image stitching. Grey graduations can be mitigated by employing a transition algorithm to adjust or otherwise reduce contrast differences between images in the series. Additional challenges are presented by the images along the bone shafts, which can lack distinguishable anatomical landmarks to assist in image stitching. To compensate for lack of landmarks along the bone shafts, a reference feature, such as an x-ray ruler (e.g., a 1-mm resolution ruler), can be placed alongside the limb to assist with image stitching. Yet additional challenges can be presented at regions of a bone involving complex anatomy, such as complex adjacent bone geometries and/or further obscuration caused by adjacent soft tissue. For example, the complex anatomy adjacent the proximal femur, particularly with respect to the femoral head (e.g., adjacent pelvis geometry and soft tissue attachments) can make it difficult to obtain images of the proximal femur with sufficient clarity for image stitching. To mitigate these anatomical challenges, alternative image angles (view angles) can be employed. For example, the inventors have demonstrated that switching from anterior-posterior and/or lateral views and instead employing oblique views of the bone (e.g., femur), such as internal oblique and external oblique views along the entire length of bone, can provide images thereof with sufficient anatomical clarity for stitching. Step 306 can include additional enhancement substeps. For example, as shown in FIG. 4, a stitched image series (e.g., any of the first, second, third, and/or fourth image series) can be subjected to a masking step, such as by overlaying a mask over the stitched image series in a manner masking the anatomy adjacent the bone. This can further reduce image noise, such as by removing non-bone features from the images, such as implants, instrumentation, other hardware, and the like.

The image enhancements of step 306 can produce enhanced versions of the first and second representations 5, 5', such as enhanced versions of the stitched image series thereof (e.g., enhanced versions of the first, second, third, and/or fourth image series). It should be appreciated that the stitched, enhanced versions of the first and second image series can be referred to, respectively, as first and second enhanced 2D images of the fractured bone 1. The stitched, enhanced versions of the third and fourth image series can be referred to, respectively, as third and fourth enhanced 2D images of the contralateral bone 1'. Additionally, or alternatively, step 306 can comprise generating sets of digital data from the first, second, third, and fourth enhanced 2D images that characterize shapes and/or other geometric features of the fractured bone 1 and contralateral bone 1'. The image enhancements of step 306 can facilitate the use of the first representation 5 of the fractured bone 1 and the second representation 5' of the contralateral bone 1' for creation of respective 3D models of the fractured bone 1 and contralateral bone 1'.

The method 300 comprises a step 308 of creating a first 3D virtual model of the fractured bone 1 based on one or both of the first and second enhanced 2D images of the fractured bone 1. The first 3D virtual model preferably accurately depicts the fractured portions of the bone 1, including the proximal and distal bone fragments 3, 4. Step 308 can also comprise creating a second 3D virtual model of the contralateral bone 1' based on one or both of the third and fourth enhanced 2D images of the contralateral bone 1'. Creating the first and second 3D virtual models can be performed with the assistance of one or more artificial intelligence (AI) programs executing algorithms, such as machine learning algorithms and/or deep learning algorithms, for comparing the first and second enhanced 2D images against a vast digital library of images of the subject bones (e.g., femurs, tibias, etc.). The library images can include entire renditions of a subject bone or portions thereof. The algorithms (e.g., machine learning) can assist the AI program(s) in creating the first and second 3D virtual models based on the information (i.e., visual information and/or sets of digital data) depicted in the first and second enhanced 2D images. For example, the AI program(s) can employ deep learning algorithms that train a neural network to reconstruct a respective 3D point cloud from each of the first and second enhanced 2D images. The respective 3D point clouds can then be further constructed (e.g., with the assistance of a computer-aided design (CAD) program) into respective 3D meshes that constitute the first and second 3D virtual models.

Figure 5B:
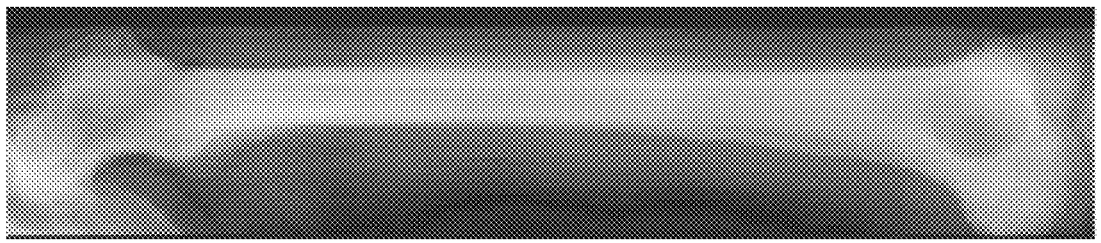
FIG. 5B shows an example of another rendition of the 3D model of a femur shown in FIG. 5A, as a step of the example method illustrated in FIG. 3A.
Figure 5A:
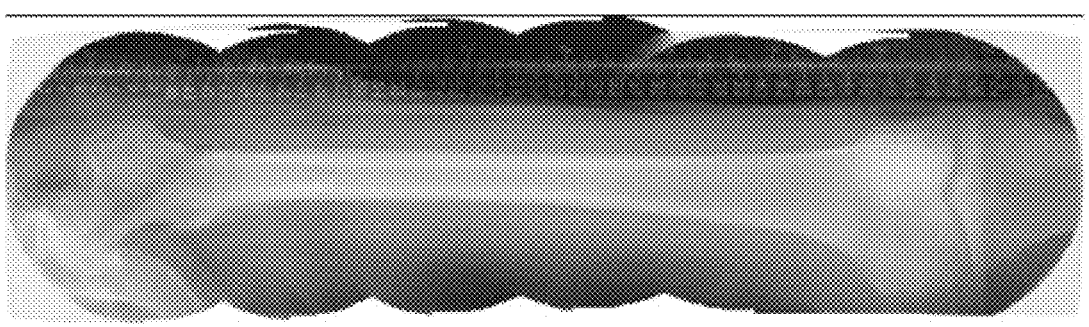
FIG. 5A shows an example rendition of 3D model of a femur generated from data presented in the medical imagery of the present disclosure, as a step of the example method illustrated in FIG. 3A.

Step 308 can include rendering the first and second 3D virtual models "on top of" the respective stitched images, an example of which is shown in FIG. 5A. Additionally or alternatively, step 308 can include rendering the first and second 3D virtual models as respective overlays in the respective stitched images, an example of which is shown in FIG. 5B. These additional rendering substeps of step 308 can be employed to assess the geometric accuracy of the first and second 3D virtual models, and can be employed as iterative steps that can be repeated with certain adjustments to enhance the accuracy of the respective 3D virtual models. Step 308 can include outputting the finalized first and second 3D virtual models, which can then be employed as needed to calculate parameters for assisting with a repair of the fractured bone 1. FIGS. 6A-6E depicts various views of a 3D virtual model 10' of an intact femur output during step 308. FIGS. 7A-7E depicts various views of a 3D virtual model 10' of an intact tibia output during step 308. In other embodiments, one or both of the 3D virtual model 10, 10' of the fractured bone 1 and contralateral bone 1' can be a 3D CT construct, such as when the second and/or fourth image series includes CT slices taken along the length of the bone, as described above. In further embodiments, step 308 can include generating multiple 3D virtual models for each of the fractured bone 1 and contralateral bone 1'. By way of a non-limiting example of such further embodiments, step 308 can include generating a mesh-type 3D virtual model and a 3D CT construct-type model for each of the fractured bone 1 and contralateral bone 1'.

It should be appreciated that at least a portion (i.e., one or more sub-steps) of step 308 can optionally be performed by a second computing system 78. In such embodiments, computing system 76 can be referred to as the "first" computing system 76 and can be in electrical communication with the second computing system 78. For example, the second computing system 78 can be remote or "off-site" from the first computing system 76. In such embodiments, the first and second computing systems 76, 78 can be operated on separate server systems. By way of a non-limiting example, the second computing system 78, in addition to the AI program(s) and algorithms employed thereby, can be based on those developed by Zebra Medical Vision Ltd., located in Shefayim, Israel. For example, the techniques for creating mesh-types of the first and second 3D virtual models based on the respective 2D images can be similar to those more fully described in U.S. Pat. No. 10,867,436 B2, issued Dec. 15, 2020, entitled "SYSTEMS AND METHODS FOR RECONSTRUCTION OF 3D ANATOMICAL IMAGES FROM 2D ANATOMICAL IMAGES" (hereinafter, "the '436 Reference"), the entire disclosure of which is hereby incorporated by reference herein.

It should further be appreciated that the aforementioned creation of the 2D bone representations (such as those shown in FIG. 3C and FIG. 4) and the 3D virtual models of the bones is preferably completed intraoperatively, in real-time, thereby providing significant advantageous for completing a bone reduction, including for evaluating in real-time potential malalignment parameters with sufficient speed to correct or at least significantly mitigate one or more and up to all of such malalignment parameters intraoperatively. In this manner, the methods and steps described herein can significantly improve patient care in the short-term and long-term.

The method 300 comprises a step 310 of calculating one or more malalignment parameters for the fractured bone 1. The one or more malalignment parameters can be calculated by comparing corresponding alignment parameters of the fractured bone 1 and contralateral bone 1'. The one or more alignment parameters for the fractured bone 1 can be calculated from one or more of the first representation 5, the first and second enhanced 2D images, and the first 3D virtual model 10 of the fractured bone 1. The one or more alignment parameters for the contralateral bone 1' can be calculated from one or more of the second representation 5', the third and fourth enhanced 2D images, and the second 3D virtual model 10' of the contralateral bone 1'. The alignment parameters can include a dimensional parameter, such as length L1, of the respective bone 1, 1', as measured between anatomical landmarks thereof. The alignment parameters can also include one or more orientation parameters. One such orientation parameter can be angulation A1 of the bone or fragment thereof relative to a reference axis. Another such orientation parameter can be rotation or "torsion" A2 of the bone or fragment thereof about a reference axis. Each malalignment parameter can reflect a difference between the respective alignment parameters of the fractured bone 1 and contralateral bone 1', as represented by the first 3D virtual model 10 of the fractured bone 1 (which can also be referred to as the "fractured bone model" 10) and the second 3D virtual model 10' of the contralateral bone 1' (which can also be referred to as the "contralateral bone model" 10')

The method 300 comprises a step 312 of assessing whether the one or more malalignment parameters of the fractured bone 1 are within acceptable limits, which limits can be determined by the treating physician based on a number of factors, such as the severity of the fracture, location of the fracture (e.g., whether intra-articular or shaft fracture), the implant types and techniques employed to reduce the fracture, estimated impact on adjacent soft tissue, post-operative treatment plans, mitigation of short- and long-term side effects, and patient age, by way of non-limiting examples. If the one or more malalignment parameters fall within acceptable limits, as determined by the surgeon, the surgeon can conclude the method 300 and finalize the surgery as needed. If one or more of the malalignment parameters fall outside acceptable limits, the surgeon can proceed to step 314, which comprises manipulating the fractured bone 1 to adjust the reduction, such as to correct such one or more malalignment parameters to within acceptable limits. After step 314, the surgeon can repeat steps 302, 306, 308, 310, and 312 to determine whether the manipulated fractured bone 1 falls within acceptable limits of the malalignment parameter(s). It should be appreciated that in such instances after step 314, the surgeon preferably need not repeat step 304 or portions of the steps 306 and 308 for the contralateral bone 1'. By correcting or otherwise bringing the malalignment parameters within acceptable limits intraoperatively, during the initial fracture reduction operation, the methods 300 and steps herein can avoid a potential need to bring the patient back in for postoperative correction(s) (which themselves can present further complications). In this manner, the methods 300 and steps herein can significantly improve the overall treatment and patient experience of a fracture reduction.

Figure 8:
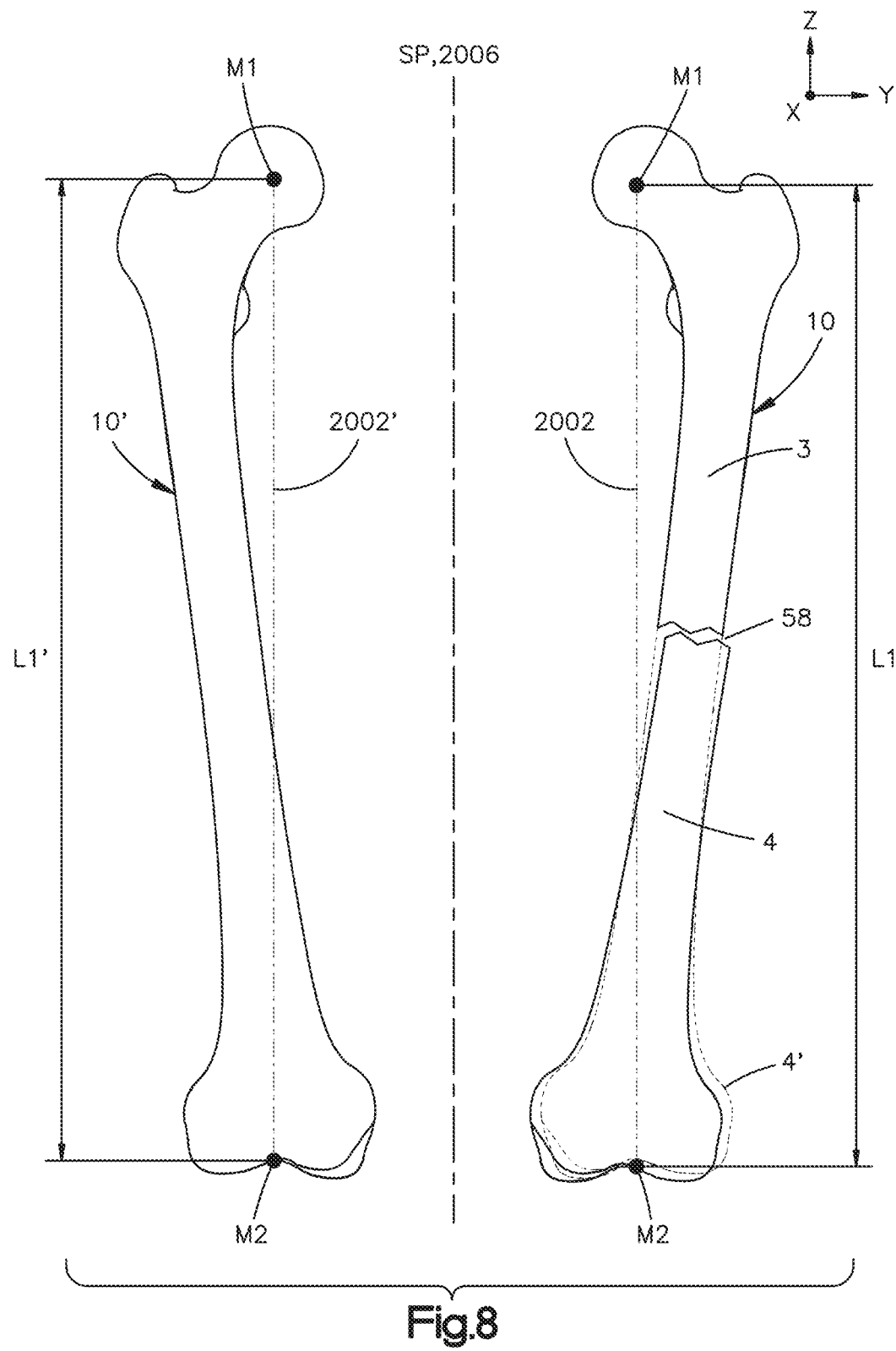
FIG. 8 shows example steps of using corresponding 3D models of a fractured bone and contralateral bone to calculate a malalignment length parameter of the fractured bone by comparison to the contralateral bone, such as during a reduction procedure, according to the example method shown in FIG. 3A.

Referring now to FIG. 8, to calculate the respective length of each bone 1, 1', corresponding anatomical landmarks (e.g., M1, M2) can be selected as references to assist the measurements with respect to the fractured bone model 10 and the contralateral bone model 10'. In the illustrated example, the proximal landmarks M1 are located at the centroid of the femoral heads 40 and the distal landmarks M2 are located at the intercondylar notches 56 of the respective fractured and contralateral bone models 10, 10'. In this particular example, the landmarks M1, M2 are positioned along the respective mechanical axes 2002, 2002' of the bone models 10, 10'. The landmarks M1, M2 can be plotted in virtual 3D space in the first and second 3D virtual models, such as with respect to a 3-axis coordinate system, such as an x,y,z cartesian coordinate system, which can be aligned with coordinate system 1000 described above with reference to FIG. 1A. The computing system 76 can plot the landmarks M1, M2 autonomously according to pre-programmed instructions. Alternatively, the surgeon can select one or more of the landmarks M1, M2. According to one such example, the system 100 can be configured to allow the surgeon to select one or both of the landmarks M1, M2, via the user interface 86, based on a list of landmarks options presented on the display 108. According to another such example, the system 100 can be configured to allow the surgeon to input one or both of the landmarks M1, M2, such as by manual input (e.g., mouse-click, stylus tap, or the like) in the 2D space of a selected image, such as an axial CT slice, obtained during step 302 and/or 304. After the corresponding landmarks M1, M2 are selected for the fractured and contralateral bone models 10, 10', the computing system 76 can calculate the respective straight line distances between the landmark M1, M2 pairs to calculate the length L1 of the fractured bone 1 and the length L1' of the contralateral bone 1'. The malalignment parameter for length, denoted herein as "ΔL," can then be derived by calculating the difference between the lengths L1, L1' of the bone models 10, 10' (ΔL=L1−L1').

It should be appreciated that, in the 3D space of each bone model 10, 10', the step of calculating the straight-line distance between the landmarks M1, M2 can include a step of identifying, for each landmark M1, M2, the respective values along the coordinate axes (in this example, the x, y, z axes). Thus, the straight-line distance between the landmarks M1, M2 in the 3D space of each bone model 10, 10' can be represented by the following equation:

$$\vec{M1} - \vec{M2} = \begin{pmatrix} M1_x \\ M1_y \\ M1_z \end{pmatrix} - \begin{pmatrix} M2_x \\ M2_y \\ M2_z \end{pmatrix}$$

Furthermore, the absolute value of the length for each bone model 10, 10', as measured between the respective landmarks M1, M2, can be represented by the following equation:

$$|\vec{L}| = \sqrt{(x_{M1}-x_{M2})^2 + (y_{M1}-y_{M2})^2 + (z_{M1}-z_{M2})^2}$$

In this manner, the respective lengths L1, L1' of each bone model 10, 10' can be calculated in 3D space, even should the landmarks reside in different planes along the x-axis (anterior-posterior direction), for example.

Figure 9A:
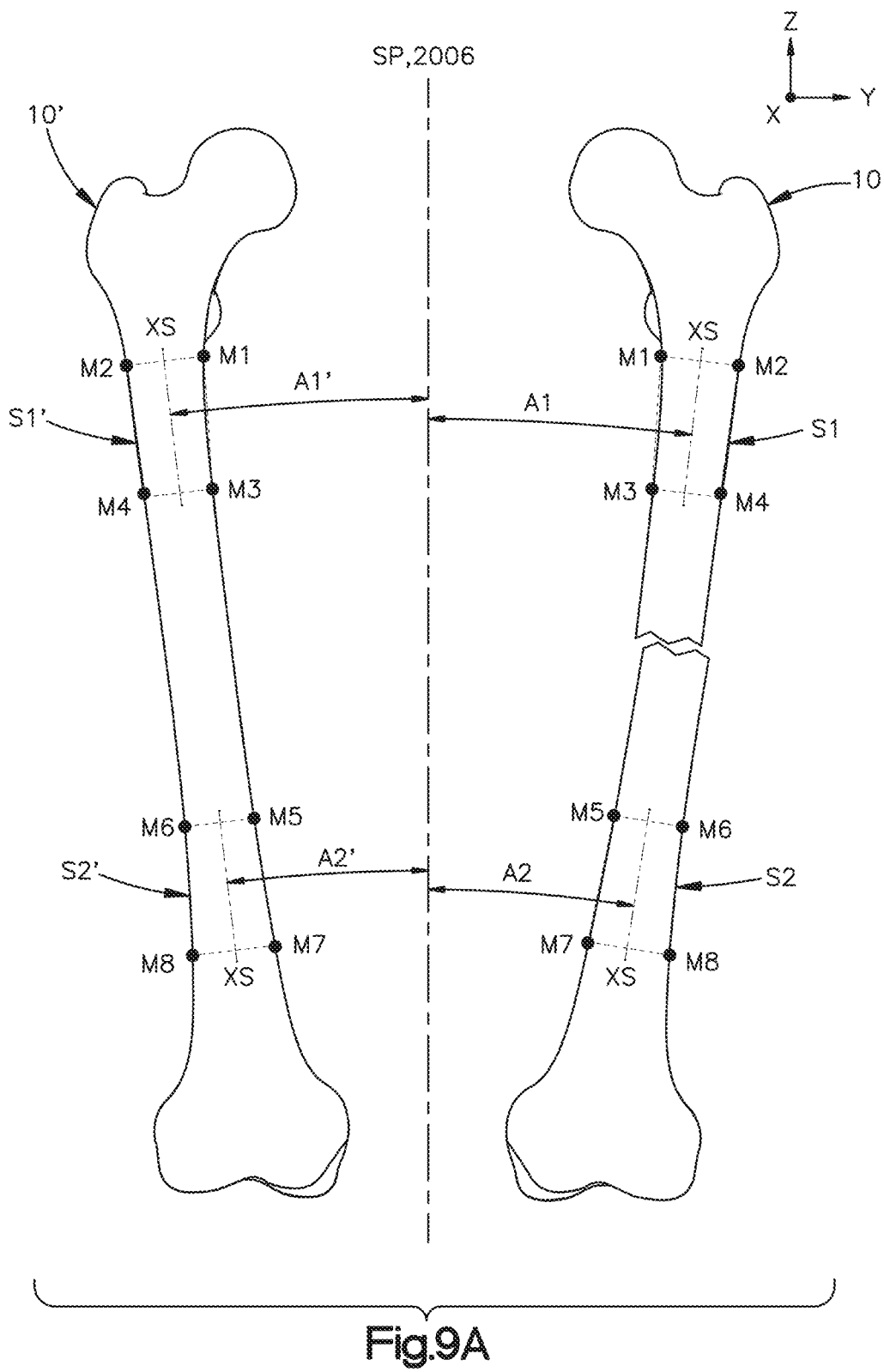
FIGS. 9A-9B show example steps of using corresponding 3D models of the fractured bone and contralateral bone to calculate a malalignment angulation parameter of the fractured bone by comparison to the contralateral bone, according to the example method shown in FIG. 3A.

Referring now to FIG. 9A, to calculate the respective angulations AI of the fragments 3, 4 of the fractured bone model 10 and the associated portions of the contralateral bone model 10' in a first reference plane, corresponding anatomical landmarks (e.g., M1-M8) can be selected as reference points to assist the measurements. The landmarks M1-M8 employed for angulation measurements according to this example are preferably located at the outer surfaces of the bone models 10, 10'. Thus, the computing system 76 can generate an outline 64 of each bone 10, 10' in the first reference plane, which in the coronal plane in this example. The landmarks M1-M8 can then be located on the outline 64. The landmarks M1-M8 can be employed in sets M1-M4 and M5-M8 on the outline 64 of each bone model 10, 10' so that each set M1-M4, M5-M8 approximates a respective reference shape S1, S2, S1', S2', having a geometry similar to that of the associated portion of the bone model 10, 10'. For example, a first set of landmarks M1-M4 can be plotted on the outline of the proximal fragment 3 and a second set of landmarks M5-M8 can be plotted on the outline of the distal fragment 4 of the fractured bone 1. Corresponding sets of landmarks M1-M4, M5-M8 can be plotted on corresponding locations of the outline of the contralateral bone 1'. In this example, the reference shapes are conical frustums, which the inventors have discovered to be advantageous for approximating segments of the bone shaft using the methods described herein. Each conical frustum extends from a base to a cap along a cone axis XS. As shown, the cone axes XS can provide a substantially accurate approximation of the position and orientation of the anatomical axes of the respective portions of the bone models 10, 10'. The conical frustums S1, S2, S1', S2' can be those of a circular cone or an elliptical cone, based on the adjacent bone geometry. The base and cap of the conical frustum S1, S2, S1', S2' can be orthogonal to or oblique to the cone axis XS. In the 2D space of the first reference plane, the reference shape S1, S2, S1', S2' is represented as a cross-section of the conical frustum, preferably taken along the cone axis XS. It should be appreciated that the conical frustums S1, S2, S1', S2' are also depicted as respective trapezoids in the first reference plane.

After the landmarks are plotted and the reference shapes are generated, the computing system 76 can employ the reference shapes S1, S2, S1', S2' to calculate their respective angulation with respect to a reference axis. In this example, the reference axis can be a common reference axis, such as the central longitudinal axis 2006. In this manner, an angulation A1 of the proximal bone fragment 3 can be calculated by measuring the angle between the central longitudinal axis 2006 and the cone axis XS of shape S1 in the reference plane. Similarly, an angulation A2 of the distal bone fragment 4 can be calculated by measuring the angle between the central longitudinal axis 2006 and the cone axis XS of shape S2. Comparative angulations A1' and A2' of the contralateral bone 1' can be calculated by measuring the angles between the central longitudinal axis 2006 and the cone axes XS of shapes S1', S2', respectively. The malalignment parameters for angulation in the first reference plane, denoted herein as "ΔA1" and "ΔA2," can then be derived for the proximal and distal bone fragments 3, 4, by calculating the differences between the their respective angulations A1, A2 and the corresponding angulations A1', A2' of the contralateral bone 1' (ΔA1=A1−A1'; ΔA2=A2−A2').

Figure 9B:
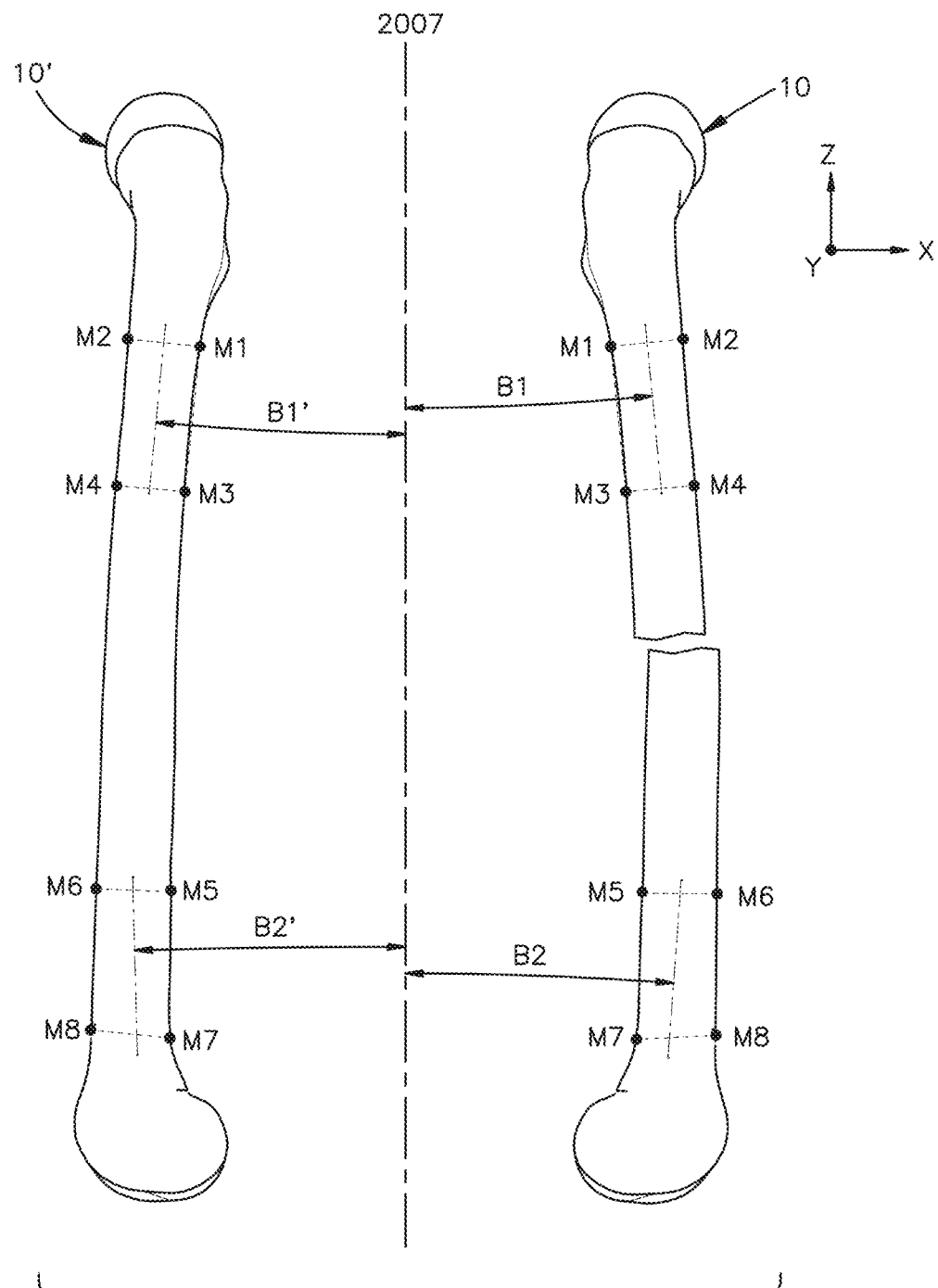

Referring now to FIG. 9B, respective angulations B1 of each bone model 10, 10' in a second reference plane can be calculated in a similar fashion that described above for the first reference plane. The second reference plane is preferably substantially perpendicular to the first reference plane, although other orientations, such as oblique orientations, including internal oblique and external oblique orientations, are within the scope of the present disclosure. In the illustrated example, the second reference plane is essentially a composite view showing the fractured bone 1 and the contralateral bone 1' each in a respective view taken in a medial-to-lateral direction from the sagittal plane. As above, the computing system 76 can generate an outline 64 of each bone model 10, 10' in the second reference plane and can plot sets of landmarks M1-M4 and M5-M8 on the outline 64 of each bone model 10, 10' so that each set M1-M4, M5-M8 approximates a respective reference shape S1, S2, S1', S2' (e.g., conical frustums) having a geometry similar to that of the associated portion of the bone model 10, 10'. As above, the cone axes XS can provide a substantially accurate approximation of the position and orientation of the anatomical axes of the respective portions of the bone models 10, 10'.

The computing system 76 can employ the reference shapes S1, S2, S1', S2' to calculate their respective angulation with respect to a reference axis. In this example, the reference axis can be a second reference axis 2007 that is parallel with the central longitudinal axis 2006 and extends along the sagittal plane at a location offset in the posterior direction. In this manner, the second reference axis 2007 can be substantially equidistantly spaced from the fractured bone 1 and the contralateral bone 1'. In the second reference plane, an angulation B1 of the proximal bone fragment 3 can be calculated by measuring the angle between the axis 2007 and the cone axis XS of shape S1; and an angulation B2 of the distal bone fragment 4 can be calculated by measuring the angle between axis 2007 and the cone axis XS of shape S2. Comparative angulations B1' and B2' of the contralateral bone 1' can be calculated by measuring the angles between the axis 2007 and the cone axes XS of shapes S1', S2', respectively. The malalignment parameters for angulation in the second reference plane, denoted herein as "ΔB1," and "ΔB2," can then be derived for the proximal and distal bone fragments 3, 4, by calculating the differences between the their respective angulations B1, B2 and the corresponding angulations B1', B2' of the contralateral bone 1' (ΔB1=B1-B1'; ΔB2=B2-B2').

It should be appreciated that malalignment parameters for angulation of the fractured bone 1 can be calculated using 3D versions of references shapes (e.g., S1, S2, S1', S2'), such as the conical frustums described above. For example, the computing system 76 can fit 3D conical frustums S1, S2 to select portions of the shafts of the proximal and distal bone fragments 3, 4 of the first 3D virtual model of the fractured bone 1. Subsequently, conical frustums S1', S2' can be fitted to corresponding portions of the shaft of the second 3D virtual model of the of the contralateral bone 1'. Fitting the conical frustums can be performed using a shape matching algorithm, a best fit algorithm, or any suitable algorithm. The angle of the cone axis of each conical frustum S1, S2, S1', S2' can be calculated in 3D space, such as with respect to a 3-axis coordinate system, such as the cartesian coordinate system described above. The malalignment parameters for angulation in the 3D space can then be derived for the proximal and distal bone fragments 3, 4, by calculating the differences between their respective cone axis angles and the corresponding cone axis angles of the conical frustums fitted on the contralateral bone 1'.

Referring now to FIGS. 10A-10E, to calculate the respective torsion angles of the fractured bone 1 and the contralateral bone 1', a reference plane RPT can be selected for the torsion measurements. In the illustrated example, the transverse plane is employed for the torsion measurements. On each of the fractured and contralateral bone models 10, 10', a first or proximal set of landmarks M1, M2 can be plotted on the proximal femur at corresponding locations to define a proximal reference axis 70, and a second or distal set of landmarks M3, M4 can be plotted on the distal femur at corresponding locations to define a distal reference axis 72. The proximal and distal reference axes 70, 72 of each bone model 10, 10' can be projected onto the torsional reference plane. A respective torsion value T1, T1' for each bone model 10, 10' can be calculated by measuring the angle between the projections of the proximal and distal axes 70, 72 in the torsional reference plane. The malalignment parameter for torsion, denoted herein as "ΔT," can then be derived by calculating the difference between the torsion angles T1, T1' of the bone models 10, 10' (ΔT=T1-T1').

According to one example, proximal landmark M1 can be located at a centroid of the femoral head, as identified in an axial image or slice 74 along a plane parallel with the transverse plane. For example, the axial image used for proximal landmark M1 can be taken along the "head center" plane, as shown in FIG. 10B. Proximal landmark M2 can be located at a centroid of the greater trochanter 44, as viewed in an axial image or slice 74 in the Waidelich or Murphy plane. In the illustrated example, the distal landmarks M3, M4 can be located on the posterior apices of the medial and lateral condyles 50, 52, as identified in one or two axial images or slices 74 parallel with the transverse plane. Thus, the distal reference axis 72 can extend along the posterior condylar tangent line. FIGS. 10D and 10E show an example of a system display showing torsion angle measurements using the techniques described above. It should be appreciated that other locations and axial images can be used for the proximal landmarks M1, M2 and distal landmarks M3, M4.

It should be appreciated that one or more of the foregoing malalignment parameters can be omitted, or alternate malalignment parameters can be selected, based on the specific needs of the reduction. Thus, the method 300 can comprise an additional step of selecting malalignment parameters for evaluating a reduction.

It should be appreciated that the foregoing steps for calculating malalignments parameters can be employed in connection with a fractured tibia and its contralateral tibia. For example, method 300 can be employed to create one or more of reference images, enhanced 2D image sets, and/or 3D virtual models of a fractured tibia and contralateral tibia for use in calculating malalignment parameters of the fractured tibia. For example, landmarks can be input onto such reference images, 2D image sets, and/or 3D virtual models of the tibias for calculating differences in length, angulation, and torsion between the fractured tibia and contralateral tibia. According to an example of calculating the malalignment parameter for length of the tibia, the respective lengths of each of the fractured and contralateral tibia models can be measured between a proximal landmark, which can be located at the tibial plateau, and a distal landmark, which can be located at the middle of the pilon tibiale. According to an example of calculating the malalignment parameter for angulation of the tibia, the reference shapes, such as conical frustums, can be plotted along outer surfaces of corresponding portions of the tibial shaft of the fractured tibia model and contralateral tibia model, and the angles can be measured between the axes of the corresponding reference shapes on the fractured tibia model and contralateral tibia model. According to an example of calculating the malalignment parameter for torsion of the tibia, a set of proximal landmarks can be plotted along one or more axial slices of the proximal tibia to generate a proximal reference axis, the angle of which can be measured with respect to a distal reference axis that intersects a set of distal landmarks plotted along one or more axial slices of the distal tibia. It should be appreciated that one or more of the foregoing malalignment parameters for the tibia can be omitted, or alternate malalignment parameters for the tibia can be selected, based on the specific needs of the reduction.

Figures 11A, 11B:
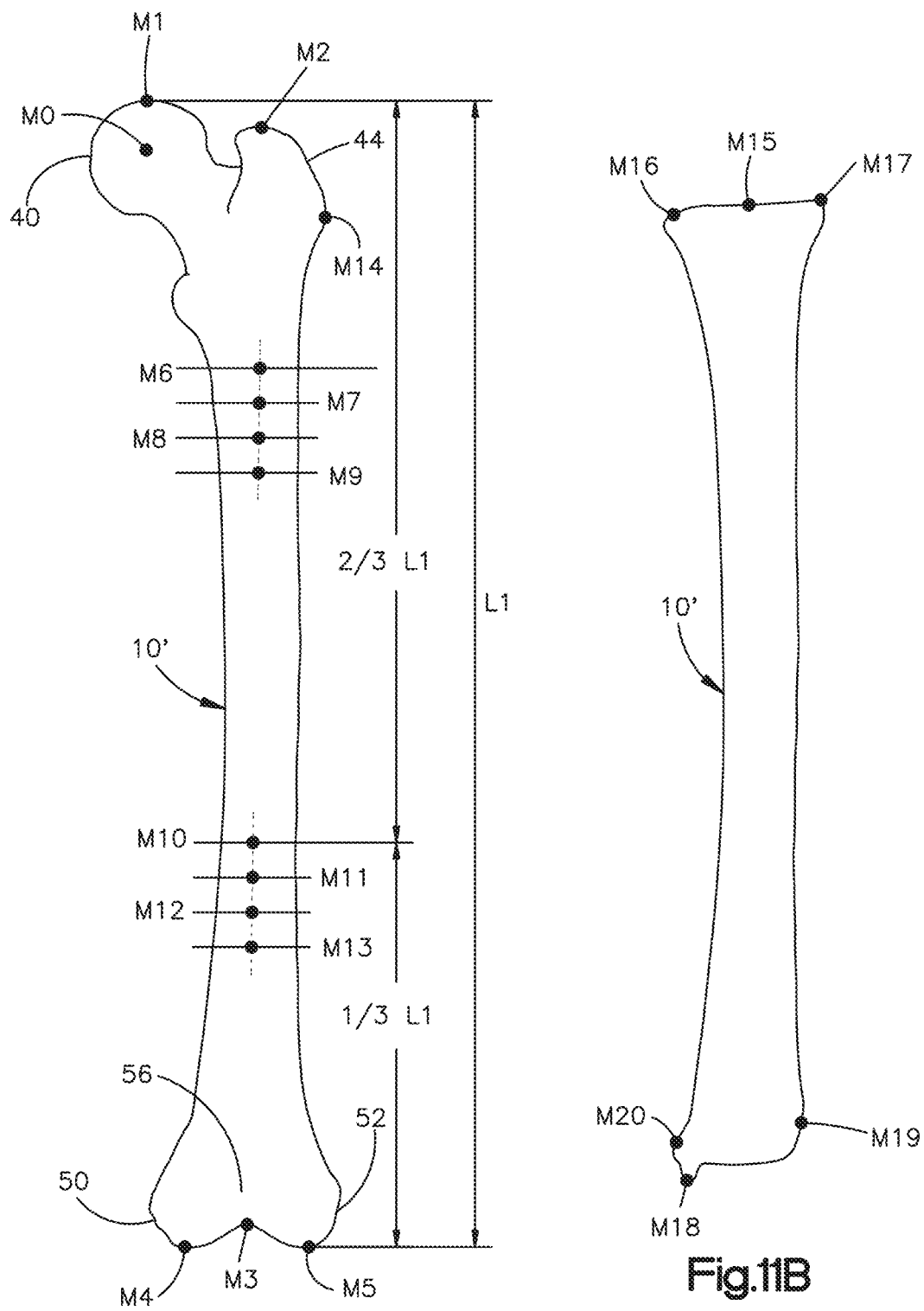
FIGS. 11A-11B show various example anatomical landmarks of a femur (FIG. 11A) and a tibia (FIG. 11B) for use in calculating malalignment parameters according to the example methods of the present disclosure.

It should be appreciated that various landmarks can be employed for calculating the malalignment parameters of a reduced bone. For example, the computing system 76 can contain a library or database of landmarks, which can be stored in the memory 82 and made available for selection to evaluate malalignments parameters of a subject bone. The landmarks of such a database can optionally have unique identification characters, such as M1-Mn, wherein "n" can represent an integer identifier for the final landmark in a set of landmarks. A non-limiting example of such a database can be organized as shown in Table 1 below, and the corresponding locations on the subject bone are shown in FIG. 11A (intact femur) and FIG. 11B (intact tibia).

TABLE 1

| MARK | BONE | LOCATION |
| --- | --- | --- |
| M0 | Femur | Midpoint of femoral head |
| M1 | Femur | Most proximal point of femoral head |
| M2 | Femur | Most proximal point of greater trochanter |
| M3 | Femur | Roof of the intercondylar fossa or notch |
| M4 | Femur | Most distal point of medial condyle |
| M5 | Femur | Most distal point of lateral condyle |
| M6 | Femur | Center point of femur shaft at the level of the most distal point of the lesser trochanter |
| M7 | Femur | Center point of femoral shaft 1 cm inferior to M6 |
| M8 | Femur | Center point of femoral shaft 1 cm inferior to M7 |
| M9 | Femur | Center point of femoral shaft 1 cm inferior to M8 |
| M10 | Femur | Center point of femoral shaft at the height of ⅓ distance between M4 and M1 |

TABLE 1-continued

| MARK | BONE | LOCATION |
| --- | --- | --- |
| M11 | Femur | Center point of femoral shaft 1 cm inferior to M10 |
| M12 | Femur | Center point of femoral shaft 1 cm inferior to M11 |
| M13 | Femur | Center point of femoral shaft 1 cm inferior to M12 |
| M14 | Femur | Most lateral point of greater trochanter, i.e. tuberculum innominatum |
| M15 | Tibia | Most proximal point of the proximal part of the tibia |
| M16 | Tibia | Most medial point surface of the proximal tibia |
| M17 | Tibia | Most lateral point of articular surface of the proximal tibia |
| M18 | Tibia | Most inferior point of the medial malleolus |
| M19 | Tibia | Most lateral point of the distal end of tibia |
| M20 | Tibia | Most medial point of the distal end of tibia |

According to the database shown in Table 1, the length of each femur model 10, 10' can be measured between any one of the proximal landmarks (M0, M1, M2, M14) and any one of the distal landmarks (M3, M4, M5). For example, in additional embodiments, the length L1 of the femur model 10, 10' can be measured between landmarks M0, M1 and M3, or between landmarks M2 and M3, or between landmarks M1 and M4, or between landmarks M1 and M5, by way of non-limiting examples. Similarly, the length of each tibia model 10, 10' can be measured between any one of the proximal landmarks (M15, M16, M17) and any one of the distal landmarks (M18, M19, M20).

Figure 12A:
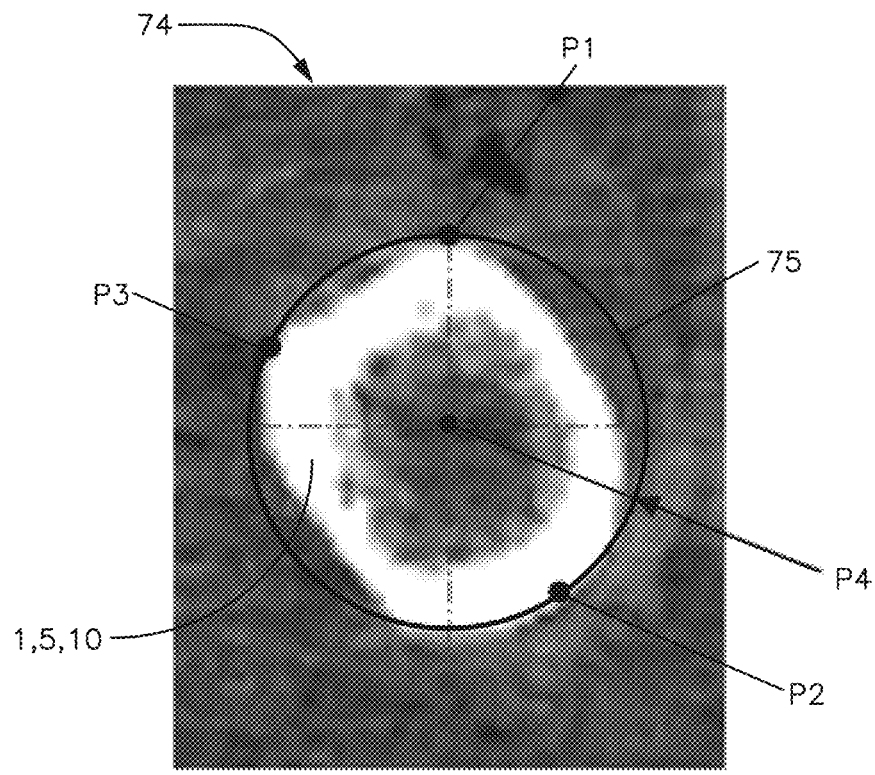
FIGS. 12A-12B show example steps of using anatomical landmarks selected from those shown in FIG. 11A to calculate a malalignment angulation parameter of a fractured bone, according to an alternative step of the method shown in FIG. 3A.
Figure 12B:
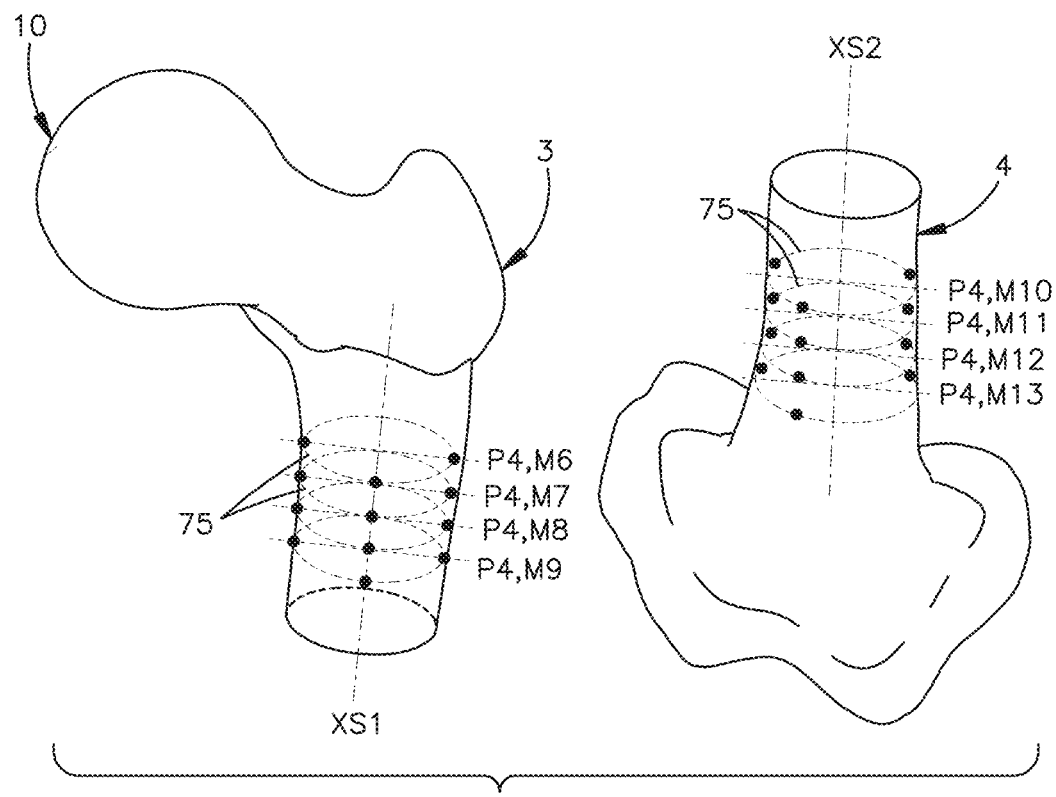

Referring now to FIGS. 12A and 12B, another example method for calculating malalignment parameters for angulation of the bone fragments 3, 4 of the fractured bone model 10 by comparison to the associated portions of the contralateral bone model 10' can include using proximal landmarks M6-M9 and distal landmarks M10-M13 from Table 1 to generate approximations of the associated anatomical axes of the bone models 10, 10'. In this example, at each of landmarks M6-M13, the computing system 76 can generate an axial image or slice 74 of the bone model 10, 10'. Alternatively, at each of landmarks M6-M13, the computing system 76 can retrieve an axial image or slice 74 of the bone 1, 1', particularly if the first and/or second representations 5, 5' of the bones 1, 1' include axial images, such as CT or MRI images.

Referring now to FIG. 12A, in each axial slice 74, the computing system 76 can generate a reference circle 75, such as by locating three (3) reference points P1, P2, P3 on the outer surface of the bone 1 and generating the reference circle 75 to intersect each of the reference points P1, P2, P3. With the reference circle 75 generated, the computing system 76 can identify the center point P4 thereof.

Referring now to FIG. 12B, for the axial slices corresponding to respective proximal landmarks M6-M9 of the bone models 10, 10', the computing system 76 can plot a proximal reference axis XS2 in 3D space that substantially intersects the center points P4 of the reference circles 75, such as by calculating a linear regression line for the proximal reference axis XS1 for each bone model 10, 10'. In similar fashion, for the axial slices 74 corresponding to respective distal landmarks M10-M13 of the bone models 10, 10', the computing system 76 can plot a distal reference axis XS2 in 3D space that substantially intersects the center points P4 of the reference circles, 75 such as along a linear regression line. To compare the angulation of the proximal bone fragment 3 with that of the associated portion of the contralateral bone model 10', the computing system 76 can calculate the difference between the respective orientations of proximal reference axes XS1 in 3D space. To compare the angulation of the distal bone fragment 4 with that of the associated portion of the contralateral bone model 10', the computing system 76 can calculate the difference between the respective orientations of distal reference axes XS2 in 3D space.

It should also be appreciated that the methods described above, including method 300 and its substeps, can be employed in connection with other bones, including other long bones (e.g., fibula, humerus, radius, and ulna), including for creating one or more of reference images, enhanced 2D image sets, and/or 3D virtual models for said other bones, including for comparative measurements with contralateral counterparts of said bones, including for calculating malalignment parameters between the counterparts, such as for evaluating a reduction of said bones.

It should be noted that the illustrations and descriptions of the examples and embodiments shown in the figures are for exemplary purposes only, and should not be construed limiting the disclosure. One skilled in the art will appreciate that the present disclosure contemplates various embodiments. Additionally, it should be understood that the concepts described above with the above-described examples and embodiments may be employed alone or in combination with any of the other examples and embodiments described above. It should further be appreciated that the various alternative examples and embodiments described above with respect to one illustrated embodiment can apply to all examples and embodiments as described herein, unless otherwise indicated.

Conditional language used herein, such as, among others, "can," "could," "might," "may," "e.g.," and the like, unless specifically stated otherwise, or otherwise understood within the context as used, is generally intended to convey that certain embodiments include, while other embodiments do not include, certain features, elements, and/or steps. Thus, such conditional language is not generally intended to imply that features, elements, and/or steps are in any way required for one or more embodiments or that one or more embodiments necessarily include logic for deciding, with or without author input or prompting, whether these features, elements and/or steps are included or are to be performed in any particular embodiment. The terms "comprising," "including," "having," and the like are synonymous and are used inclusively, in an open-ended fashion, and do not exclude additional elements, features, acts, operations, and so forth.

While certain example embodiments have been described, these embodiments have been presented by way of example only and are not intended to limit the scope of the inventions disclosed herein. Thus, nothing in the foregoing description is intended to imply that any particular feature, characteristic, step, module, or block is necessary or indispensable. Indeed, the novel methods and systems described herein may be embodied in a variety of other forms; furthermore, various omissions, substitutions, and changes in the form of the methods and systems described herein may be made without departing from the spirit of the inventions disclosed herein. The accompanying claims and their equivalents are intended to cover such forms or modifications as would fall within the scope and spirit of certain of the inventions disclosed herein.

It should be understood that the steps of the exemplary methods set forth herein are not necessarily required to be performed in the order described, and the order of the steps of such methods should be understood to be merely exemplary. Likewise, additional steps may be included in such methods, and certain steps may be omitted or combined, in methods consistent with various embodiments of the present invention.

Although the elements in the following method claims, if any, are recited in a particular sequence with corresponding labeling, unless the claim recitations otherwise imply a particular sequence for implementing some or all of those elements, those elements are not necessarily intended to be limited to being implemented in that particular sequence.

It should be appreciated that the subject matter presented herein may be implemented as a computer process, a computer-controlled apparatus, or a computing system or an article of manufacture, such as a computer-readable storage medium. Those skilled in the art will also appreciate that the subject matter described herein may be practiced on or in conjunction with other computer system configurations beyond those described herein, including multiprocessor systems, microprocessor-based or programmable consumer electronics, minicomputers, mainframe computers, handheld computers, personal digital assistants, e-readers, cellular telephone devices, special purposed hardware devices, network appliances, and the like. The embodiments described herein may also be practiced in distributed computing environments, where tasks are performed by remote processing devices that are linked through a communications network. In a distributed computing environment, program modules may be located in both local and remote memory storage devices.

Each of the processes, methods, and algorithms described in the preceding sections may be embodied in, and fully or partially automated by, code modules executed by one or more computers or computer processors. The code modules may be stored on any type of non-transitory computer-readable medium or computer storage device, such as hard drives, solid state memory, optical disc, and/or the like. The processes and algorithms may be implemented partially or wholly in application-specific circuitry. The results of the disclosed processes and process steps may be stored, persistently or otherwise, in any type of non-transitory computer storage such as, e.g., volatile or non-volatile storage.

What is claimed:

1. A method, comprising:
    imaging, intraoperatively, a fractured bone of a patient to obtain a representation of the fractured bone in a computing system, the fractured bone defining at least a first bone fragment, and a second bone fragment that is separated from the first bone fragment by a fracture;
    imaging a contralateral bone of the patient to obtain a representation of the contralateral bone in the computing system;
    generating, intraoperatively in the computing system:
        a 3D virtual model of the fractured bone from data presented in the representation of the fractured bone; and
        a 3D virtual model of the contralateral bone from data presented in the representation of the contralateral bone
    comparing, intraoperatively in the computing system,
        a first spatial dimension measured in the 3D virtual model of the fractured bone in the computing system, with
        a second spatial dimension measured in the 3D virtual model of the contralateral bone.

2. The method of claim 1, wherein the comparing step comprises calculating a difference in value between the first spatial dimension and the second spatial dimension.

3. The method of claim 2, further comprising displaying the difference in value on a display device intraoperatively.

4. The method of claim 3, further comprising manipulating at least one of the first and second bone fragments relative to the other of the first and second bone fragments, thereby reducing the difference in value.

5. The method of claim 1, further comprising comparing, intraoperatively in the computing system:
    a third spatial dimension measured in one of the 3D virtual model of the fractured bone and the representation of the fractured bone in the computing system, with
    a fourth spatial dimension measured in one of the 3D virtual model of the contralateral bone and the representation of the contralateral bone, wherein the third and fourth spatial dimensions are distinct from the first and second spatial dimensions, respectively.

6. The method of claim 5, wherein the step of comparing the third spatial dimension with the fourth spatial dimensions comprises calculating a difference in value between the third spatial dimension and the fourth spatial dimension.

7. The method of claim 6, further comprising comparing, intraoperatively in the computing system:
    a fifth spatial dimension measured in one of the 3D virtual model of the fractured bone and the representation of the fractured bone in the computing system, with
    a sixth spatial dimension measured in one of the 3D virtual model of the contralateral bone and the representation of the contralateral bone, wherein the fifth and sixth spatial dimensions are distinct from the third and fourth spatial dimensions and the first and second spatial dimensions, respectively.

8. The method of claim 7, wherein the step of comparing the fifth spatial dimension with the sixth spatial dimension comprises calculating a difference in value between the fifth spatial dimension and the sixth spatial dimension.

9. The method of claim 8, further comprising:
    displaying the difference in value between the third and fourth spatial dimensions on a display device intraoperatively; and
    displaying the difference in value between the fifth and sixth spatial dimensions on the display device intraoperatively.

10. The method of claim 9, further comprising:
    manipulating at least one of the first and second bone fragments relative to the other of the first and second bone fragments, thereby reducing at least one of the differences in value between the third and fourth spatial dimensions and the fifth and sixth spatial dimensions.

11. The method of claim 7, wherein the first and second spatial dimensions are respective lengths of the fractured bone and the contralateral bone.

12. The method of claim 11, wherein the third spatial dimension is an angulation of one of the first and second bone fragments relative to a mechanical axis of the fractured bone, and the fourth spatial dimension is an angulation of a portion of the contralateral bone relative to a mechanical axis of the contralateral bone, wherein the portion of the contralateral bone corresponds to the one of the first and second bone fragments.

13. The method of claim 12, wherein the fifth spatial dimension is a torsion of a proximal portion of the fractured bone relative to a distal portion of the fractured bone about a mechanical axis of the fractured bone, and the sixth spatial dimension is a torsion of a proximal portion of the contralateral bone relative to a distal torsion of the contralateral bone, wherein the proximal and distal portions of the contralateral bone correspond respectively to the proximal and distal portions of the fractured bone.

14. The method of claim 1, further comprising:
- plotting a first set of landmarks in the 3D virtual model of the fractured bone, wherein the first spatial dimension is measured autonomously with respect to the first set of landmarks; and
- plotting a second set of landmarks in the 3D virtual model of the contralateral bone, wherein the second spatial dimension is measured autonomously with respect to the second set of landmarks.

15. The method of claim 14, wherein the first set of landmarks comprises a first subset of landmarks that are plotted on the first bone fragment and a second subset of landmarks that are plotted on the second bone fragment.

16. The method of claim 15, wherein the second set of landmarks comprises:
- a third subset of landmarks that are plotted autonomously in the computing system on a first portion of the contralateral bone that corresponds to the first bone fragment; and
- a fourth subset of landmarks that are plotted autonomously in the computing system on a second portion of the contralateral bone that corresponds to the second bone fragment.

17. The method of claim 15, wherein the fractured bone is a femur or tibia, the fracture is located along a shaft of the fractured bone such that each of the first and second bone fragments and first and second portions of the contralateral bone comprises a portion of the shaft, and each of the first, second, third, and fourth subset of landmarks defines a respective frustum that defines a respective frustum axis that substantially approximates an anatomical axis of the respective portion of the shaft.

18. The method of claim 17, wherein the computing system calculates a respective angulation between each frustum axis and a central longitudinal axis of patient anatomy.

19. A method, comprising:
- imaging, intraoperatively, a fractured bone of a patient to obtain a representation of the fractured bone in a computing system, the fractured bone defining at least a first bone fragment, and a second bone fragment that is separated from the first bone fragment by a fracture, wherein the representation of the fractured bone comprises a combined series of images of the fractured bone taken at intervals along a length of the fractured bone;
- imaging, intraoperatively, a contralateral bone of the patient to obtain a representation of the contralateral bone in the computing system, wherein the representation of the contralateral bone comprises a combined series of images of the contralateral bone taken at intervals along a length of the contralateral bone;
- measuring, intraoperatively in the computing system, a first spatial dimension defined with respect to at least two anatomical landmarks presented in one of the representation of the fractured bone and the representation of the contralateral bone;
- identifying, intraoperatively and automatically in the computing system, contralateral counterparts of the at least two anatomical landmarks presented in the other of the representation of the fractured bone and the representation of the contralateral bone;
- measuring, intraoperatively in the computing system, a second spatial dimension defined with respect to the contralateral counterparts of the at least two anatomical landmarks.

20. The method of claim 19, wherein the combined series of images of the fractured bone and contralateral bone each comprise a respective plurality of x-ray images stitched together in a manner depicting an entire length of the respective fractured bone and contralateral bone.

* * * * *